(12) United States Patent
Owa et al.

(10) Patent No.: US 8,807,978 B2
(45) Date of Patent: Aug. 19, 2014

(54) TEMPLATE MANUFACTURING METHOD, TEMPLATE INSPECTING METHOD AND INSPECTING APPARATUS, NANOIMPRINT APPARATUS, NANOIMPRINT SYSTEM, AND DEVICE MANUFACTURING METHOD

(75) Inventors: Soichi Owa, Kumagaya (JP); Katsura Otaki, Kamakura (JP)

(73) Assignee: Nikon Corporation, Tokyo (JP)

( * ) Notice: Subject to any disclaimer, the term of this patent is extended or adjusted under 35 U.S.C. 154(b) by 393 days.

(21) Appl. No.: 12/967,572

(22) Filed: Dec. 14, 2010

(65) Prior Publication Data

US 2011/0272382 A1 Nov. 10, 2011

Related U.S. Application Data

(63) Continuation of application No. PCT/JP2009/002504, filed on Jun. 3, 2009.

(30) Foreign Application Priority Data

Jun. 18, 2008 (JP) .................................. 2008-159045
Jun. 18, 2008 (JP) .................................. 2008-159048

(51) Int. Cl.
*C23F 1/02* (2006.01)
*C23F 1/00* (2006.01)
*B05D 3/12* (2006.01)

(52) U.S. Cl.
USPC ........ 425/169; 425/174.4; 425/385; 264/293; 264/219; 264/40.1

(58) Field of Classification Search
USPC .............. 264/293, 40.1, 219; 425/174.4, 385; 425/169; 356/237.5
See application file for complete search history.

(56) References Cited

U.S. PATENT DOCUMENTS 4,579,455 A * 4/1986 Levy et al. .................... 356/394
5,772,905 A 6/1998 Chou
7,815,824 B2 * 10/2010 Sreenivasan et al. ........ 264/40.1
(Continued)

FOREIGN PATENT DOCUMENTS

JP A-2006-521682 9/2006
JP A-2006-289684 10/2006
(Continued)

OTHER PUBLICATIONS

Written Opinion of the International Searching Authority issued in International Application No. PCT/JP2009/002504 dated Sep. 1, 2009 (with translation).

(Continued)

*Primary Examiner* — Joseph S Del Sole
*Assistant Examiner* — Nahida Sultana
(74) *Attorney, Agent, or Firm* — Oliff PLC

(57) ABSTRACT

There is provided a template inspection apparatus which inspects a replica template, manufactured by an imprinting method from a master template having a depression/protrusion pattern, the template inspection apparatus including: an inspection light source part which radiates inspection light of plane waves; a stage configured to dispose the master template and the replica template so as to be in close proximity with each other and be irradiated by the inspection light; and a detection part which detects light of a component transmitting through the master template and the replica template and different from the plane waves. Accordingly, a template can be inspected in a short time.

13 Claims, 26 Drawing Sheets

(56) References Cited

U.S. PATENT DOCUMENTS

| | | | |
|---|---|---|---|
| 8,202,463 B2* | 6/2012 | Yoneda et al. | 264/293 |
| 8,294,889 B2* | 10/2012 | Kashiwagi et al. | 356/237.2 |
| 2004/0124566 A1* | 7/2004 | Sreenivasan et al. | 264/494 |
| 2004/0192041 A1 | 9/2004 | Jeong et al. | |
| 2005/0116370 A1* | 6/2005 | Ogino et al. | 264/40.1 |
| 2006/0076717 A1* | 4/2006 | Sreenivasan et al. | 264/494 |
| 2006/0158651 A1* | 7/2006 | Watts et al. | 356/401 |
| 2007/0081154 A1* | 4/2007 | Mapoles et al. | 356/237.5 |
| 2007/0264591 A1 | 11/2007 | Wuister et al. | |
| 2009/0205658 A1* | 8/2009 | Tanaka et al. | 128/203.15 |
| 2009/0267267 A1* | 10/2009 | Yoneda et al. | 264/293 |
| 2010/0314798 A1* | 12/2010 | Kawakami | 264/293 |
| 2011/0090512 A1* | 4/2011 | Miyoshi et al. | 356/600 |
| 2013/0106023 A1* | 5/2013 | Iimura et al. | 264/406 |
| 2013/0193602 A1* | 8/2013 | Suzuki et al. | 264/40.1 |
| 2013/0207288 A1* | 8/2013 | Mikami | 264/40.1 |

FOREIGN PATENT DOCUMENTS

| | | |
|---|---|---|
| JP | A-2007-130871 | 5/2007 |
| JP | A-2007-307899 | 11/2007 |
| JP | A-2008-116272 | 5/2008 |
| WO | WO 2004/086471 A1 | 10/2004 |

OTHER PUBLICATIONS

International Search Report dated Sep. 1, 2009 in International Patent Application No. PCT/JP2009/002504 (with translation).

Jul. 29, 2013 Office Action issued in Japanese Patent Application No. 2010-517690 (with translation).

* cited by examiner

US 8,807,978 B2

TEMPLATE MANUFACTURING METHOD, TEMPLATE INSPECTING METHOD AND INSPECTING APPARATUS, NANOIMPRINT APPARATUS, NANOIMPRINT SYSTEM, AND DEVICE MANUFACTURING METHOD

FIELD OF THE INVENTION

The present invention relates to a method of manufacturing a template used in nanoimprinting. The present invention further relates to: a method of and an apparatus for inspecting a template used in nanoimprinting; a nanoimprinting apparatus; a nanoimprinting system; and a device fabricating method.

BACKGROUND ART

Accompanying the increased fineness and higher levels of integration of semiconductor integrated circuits in recent years is an increase in the accuracy with which photolithographic apparatuses, which serve as a pattern transfer technology, implement the microfabrication of such semiconductor integrated circuits. To increase the fineness and accuracy even further, technologies have been proposed to replace the photolithography technology. For example, Patent Document 1 discloses a nanoimprinting technology that transfers a prescribed pattern by stamping a setting resin, which is formed on a front surface of the substrate, with a template, whose depression/protrusion pattern is the reverse of a pattern to be formed on a substrate.

To increase productivity in such nanoimprinting technology, it is effective to use an original master template (hereinbelow, called "master template") to produce a plurality of replica templates (hereinbelow, called "replica templates") and to mount these replica templates on different nanoimprinting apparatuses. For example, Patent Document 2 discloses a manufacturing method wherein replica templates are manufactured using a master template.

[PATENT LITERATURE 1] U.S. Pat. No. 5,772,905
[PATENT LITERATURE 2] Japanese Patent Application laid-open No. 2007-130871

DISCLOSURE OF INVENTION

Technical Problem

When performing a production step using a plurality of replica templates and a nanoimprinting apparatus as discussed above, it is desirable to improve mass producibility when producing the high precision replica templates.

In addition, it is necessary to precisely manufacture the replica templates such that they correspond to the master template. When the replica templates are inspected in the conventional art, the depression/protrusion pattern of each replica template is inspected one by one via an electron microscope or based on scattered light obtained by radiating an electron beam, and this inspection requires a great deal of time.

An object of the present invention is to provide a template manufacturing method that can improve the mass producibility of replica templates. Another object of the present invention is to provide a template inspecting method and inspection apparatus that can inspect a template in a short time. Yet another object of the present invention is to provide a nanoimprinting system that uses the same.

Solution to Problem

A template manufacturing method according to a first aspect of the present invention comprises: a resin-film forming step for forming a resin film on a large substrate; an imprinting step for imprinting the resin film on the large substrate by using a small master template and in a step-and-repeat manner; an etching step for performing etching, after a pattern of the master template has been formed over the entire large substrate, for the large substrate through the resin film; a protective-layer forming step for forming, after the etching, a protective layer on the large substrate; a dicing step for dicing the large substrate into a plurality of replica templates; and a removing step for removing the protective layer from the replica template.

A template manufacturing method according to a second aspect of the present invention comprises: a dicing step for dicing a large substrate into a plurality of small substrates; a cleaning step for performing cleaning, after the dicing step, for the plurality of small substrates; a disposing step for disposing the plurality of cleaned small substrates inside a frame; a resin-film forming step for forming a resin film on each of the small substrates disposed inside the frame; an imprinting step for imprinting the resin film on each of the small substrates by using a small master template and in a step-and-repeat manner; an etching step for performing etching, after a pattern of the master template has been formed on each of the small substrates, for the small substrates via the resin films; and a removing step for removing the small substrates from the frame.

A template inspecting method according to a third aspect of the present invention is a template inspecting method for inspecting a replica template manufactured by an imprinting method from a master template having a depression/protrusion pattern. This method comprises: an approaching step for bringing the master template and the replica template into close proximity; an irradiating step for irradiating inspection light of plane waves to the master template and the replica template; and a detecting step for detecting light of a component different from the plane waves.

A template inspection apparatus according to a fourth aspect of the present invention is a template inspection apparatus which inspects a replica template manufactured by an imprinting method from a master template having a depression/protrusion pattern. This apparatus comprises: an inspection light source part which radiates inspection light of plane waves; a stage configured to dispose the master template and the replica template so as to be in close proximity with each other and be irradiated by the inspection light; and a detection part which detects light of a component transmitting through the master template and the replica template and different from the plane waves.

A nanoimprinting apparatus according to a fifth aspect of the present invention comprises: a master template which has a depression/protrusion pattern; a replica template which is manufactured from the master template by an imprinting method; an inspection light source part which radiates inspection light of plane waves; a stage configured to dispose the master template and the replica template so as to be in close proximity with each other and be irradiated by the inspection light; a detection part which detects light of a component transmitting through the master template and the replica template and different from the plane waves; a transport unit which transports the replica template in a case that the detection part determines that defects are not present in the replica template; a holding part which receives the replica template from the transport unit and which holds the replica template; a substrate mounting platform which is disposed opposing the replica template held by the holding part and whereon a substrate is mounted the substrate being coated with a liquid resin; and a pressing part which presses at least one of the replica template and the substrate such that the resin is stamped with the depression/protrusion pattern.

A nanoimprinting system according to a sixth aspect of the present invention comprises: a master template which has a depression/protrusion pattern; a replica template which is manufactured from the master template by an imprinting method; an inspection light source part which radiates inspection light of plane waves; a stage configured to dispose the master template and the replica template so as to be in close proximity with each other and be irradiated by the inspection light; a detection part which detects light of a component transmitting through the master template and the replica template and different from the plane waves; a transport unit which transports the replica template in a case that the detection part determines that defects are not present in the replica template; two holding parts which receive two pieces of the replica templates respectively from the transport unit and which hold the replica templates; two substrate mounting platforms which are disposed opposing the two replica templates held by the two holding parts and whereon substrates are mounted, each of the substrates being coated with a liquid resin; and two pressing parts each of which presses at least one of the replica template and the substrate such that the resin is stamped with the depression/protrusion pattern.

A device manufacturing method according to a seventh aspect of the present invention comprises: an inspecting step for inspecting a depression/protrusion pattern of a manufactured replica template by using the replica template inspection apparatus according to the fourth aspect of the present invention and; a stamping step for stamping a substrate, which is coated with a resin, with the depression/protrusion pattern of the replica template; and an etching step for etching the substrate using the depression/protrusion pattern in the stamped resin as a mask.

A device manufacturing method according to an eighth aspect of the present invention comprises: an inspecting step for inspecting a depression/protrusion pattern of a manufactured replica template by using the nanoimprinting apparatus according to the fifth aspect of the present invention; a stamping step for stamping a substrate, which is coated with a resin, with the depression/protrusion pattern of the replica template; and an etching step for etching the substrate using the depression/protrusion pattern in the stamped resin as a mask.

Effects of the Invention

The present invention can improve the mass producibility of replica templates. In addition, the present invention can inspect a replica template in a short time.

BRIEF DESCRIPTION OF THE DRAWINGS

FIG. 24 is a conceptual diagram that shows a second nanoimprinting apparatus 210, which has the first replica template inspection apparatus 100 built in.

BEST MODE FOR CARRYING OUT THE INVENTION

<First Nanoimprinting Apparatus 200>

Figure 1:
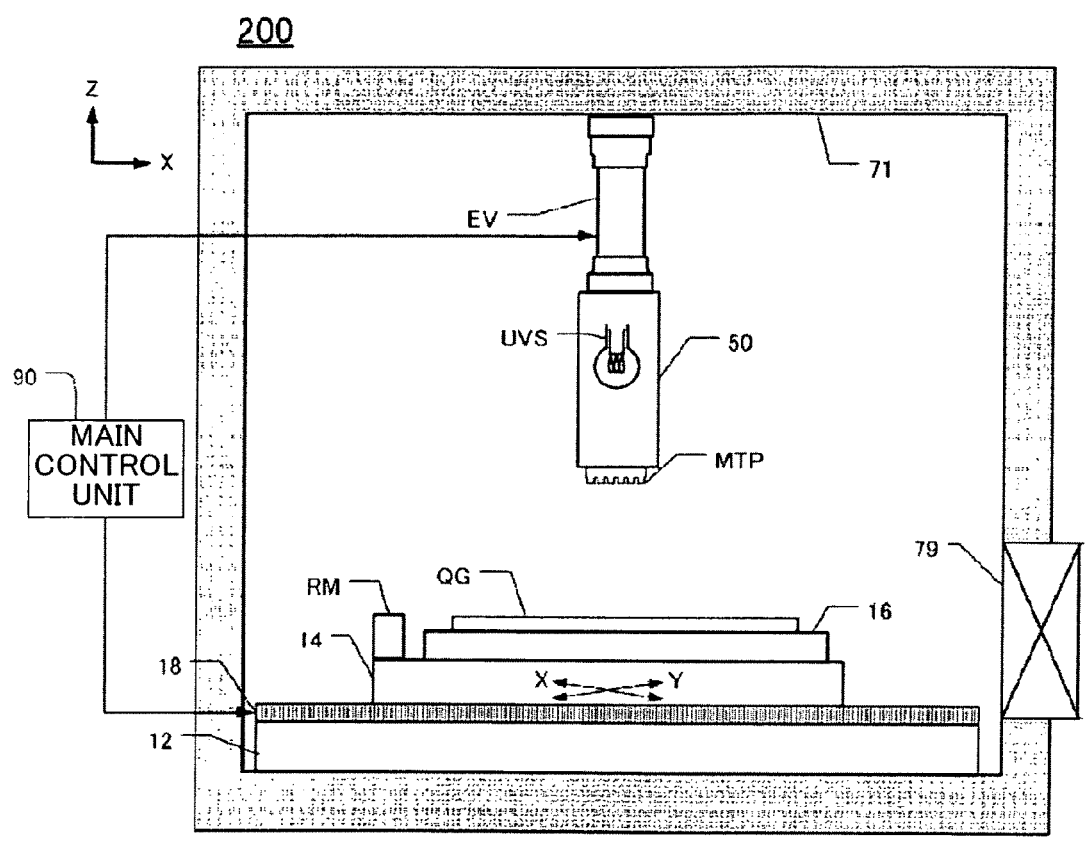
FIG. 1 is a conceptual diagram that shows a first nanoimprinting apparatus 200.

FIG. 1 is a conceptual diagram that shows a first nanoimprinting apparatus 200. The first nanoimprinting apparatus 200 can transfer a depression/protrusion pattern of a master template MTP to a quartz glass substrate QG; as shown in FIG. 1, that transfer is performed inside a chamber 71.

The first nanoimprinting apparatus 200 comprises a holding part 50, which holds the master template MTP. The master template MTP is made of quartz glass and is, for example, 25×25 mm in size. The master template MTP is supported by a pressing elevator EV. The pressing elevator EV is attached to the ceiling of the chamber 71 of the first nanoimprinting apparatus 200. The pressing elevator EV can move the master template MTP in the Z directions (i.e., the vertical directions). The pressing elevator EV can bring the master template MTP and the quartz glass substrate QG into close-proximity and thereby a depression/protrusion pattern can be transferred to a setting resin formed on the quartz glass substrate QG.

Moreover, the quartz glass substrate QG is vacuum chucked and fixed by a chucking table 16. The quartz glass substrate QG is, for example, a rectangle that is approximately 150 mm on one of its sides or a circle with a diameter of approximately 200 mm. The chucking table 16 is supported by an XY stage 14. The XY stage 14 can move in the X axial directions and the Y axial directions. The XY stage 14 is capable of moving in the X axial and Y axial directions with a maximum stroke of, for example, approximately 200 mm, and thereby the depression/protrusion pattern can be transferred from one end to the other end of the quartz glass substrate QG. A reference mirror RM that extends in the X axial directions (not shown) is fixed to part of the XY stage 14 and a reference mirror RM that extends in the Y axial directions is fixed to another part of the XY stage 14. The XY stage 14 is provided with linear motors 18, which drives the XY stage 14 in the X axial and Y axial directions. The XY stage 14 is mounted on a vibration isolating block 12 such that the XY stage 14 is not affected by external vibrations.

A laser interferometer system (not shown) comprises an X axial laser interferometer, which radiates a laser beam along the X axis to the corresponding reference mirror RM, and a Y axial laser interferometer, which radiates a laser beam along the Y axis to the corresponding reference mirror RM, and measures the X coordinate and the Y coordinate of the XY stage 14. Information about the X coordinate and the Y coordinate measured by the laser interferometer system is supplied to a main control unit 90, which controls the operation of positioning the XY stage 14 using the linear motors 18 while monitoring the supplied coordinates.

Furthermore, in FIG. 1, a configuration is adopted wherein the pressing elevator EV moves the master template MTP vertically and the quartz glass substrate QG is mounted on the XY stage 14 and moved in the X axial and Y axial directions; however, configuration may be adopted wherein the master template MTP moves in the X axial and Y axial directions and the pressing elevator EV moves the quartz glass substrate QG vertically. The chamber 71 of the first nanoimprinting apparatus 200 comprises a gate 79, and the quartz glass substrate QG is loaded into and unloaded from the first nanoimprinting apparatus 200 through the gate 79.

The first nanoimprinting apparatus 200 forms replica templates by cutting the quartz glass substrate QG, whereto the depression/protrusion pattern was transferred, using a laser saw, a dicing saw, or the like.

Figure 2:
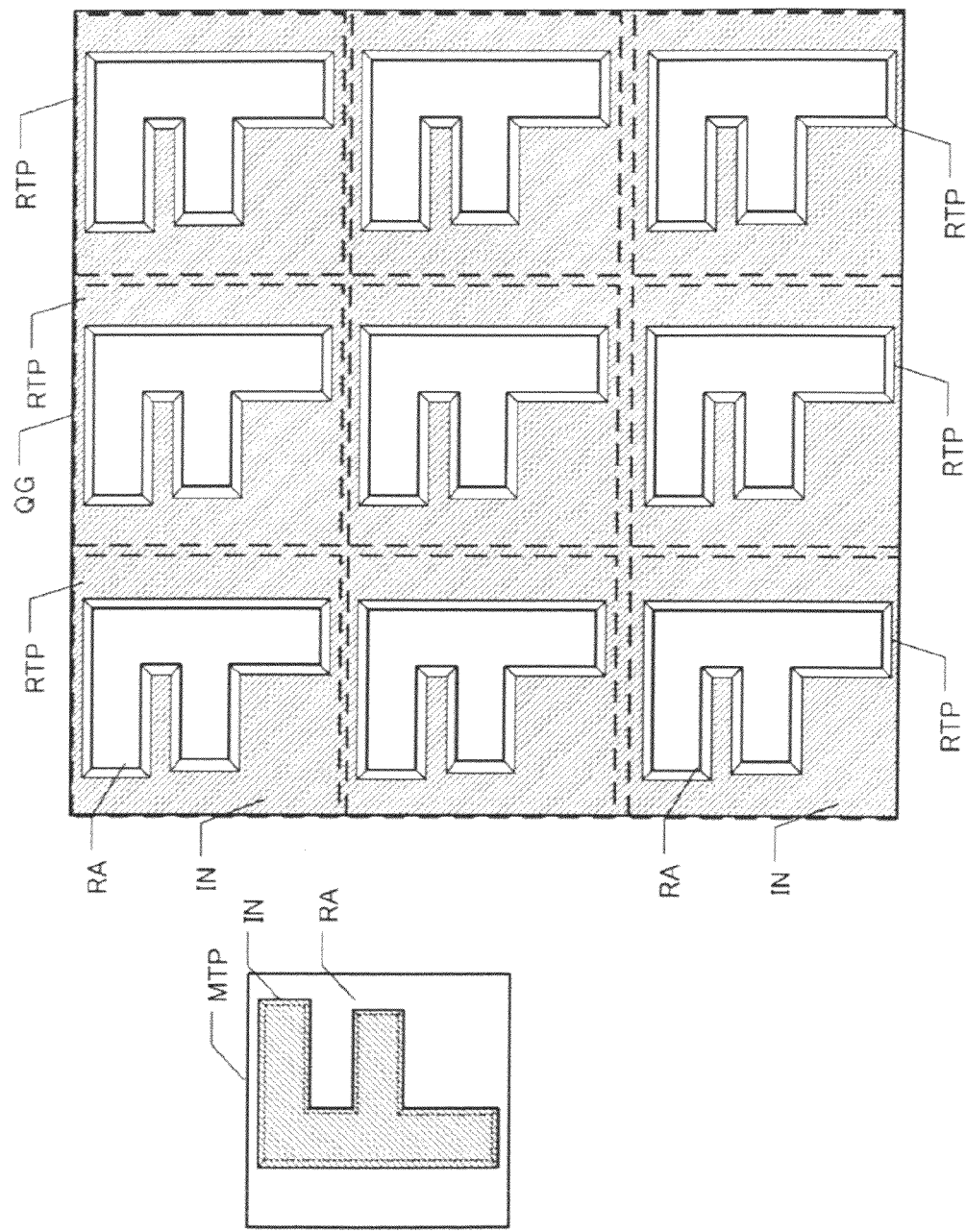
FIG. 2 is a drawing that shows the relationship between a master template MTP and replica templates RTP.

FIG. 2 shows the relationship between the master template MTP and replica templates RTP. For the sake of explanatory convenience, FIG. 2 shows F-shaped circuit patterns with depressions and protrusions. The line width of an actual pattern is approximately several tens of nanometers. Nine of the replica templates RTP are drawn in the quartz glass substrate QG; however, in actuality, for example, 64 of the replica templates RTP are manufactured. In addition, the dotted lines are scribe lines along which the laser saw, the dicing saw, or the like cuts.

As shown in FIG. 2, the depression/protrusion pattern of the master template MTP comprises a protruding area RA and a depressed area IN. When the master template MTP stamps the setting resin on each of the quartz glass substrates QG, a mirror image of the F-shaped depression/protrusion pattern is formed on the quartz glass substrate QG, namely, the protruding area RA and the depressed area IN is formed in reverse.

<Production of the Master Template MTP>

Figure 3:
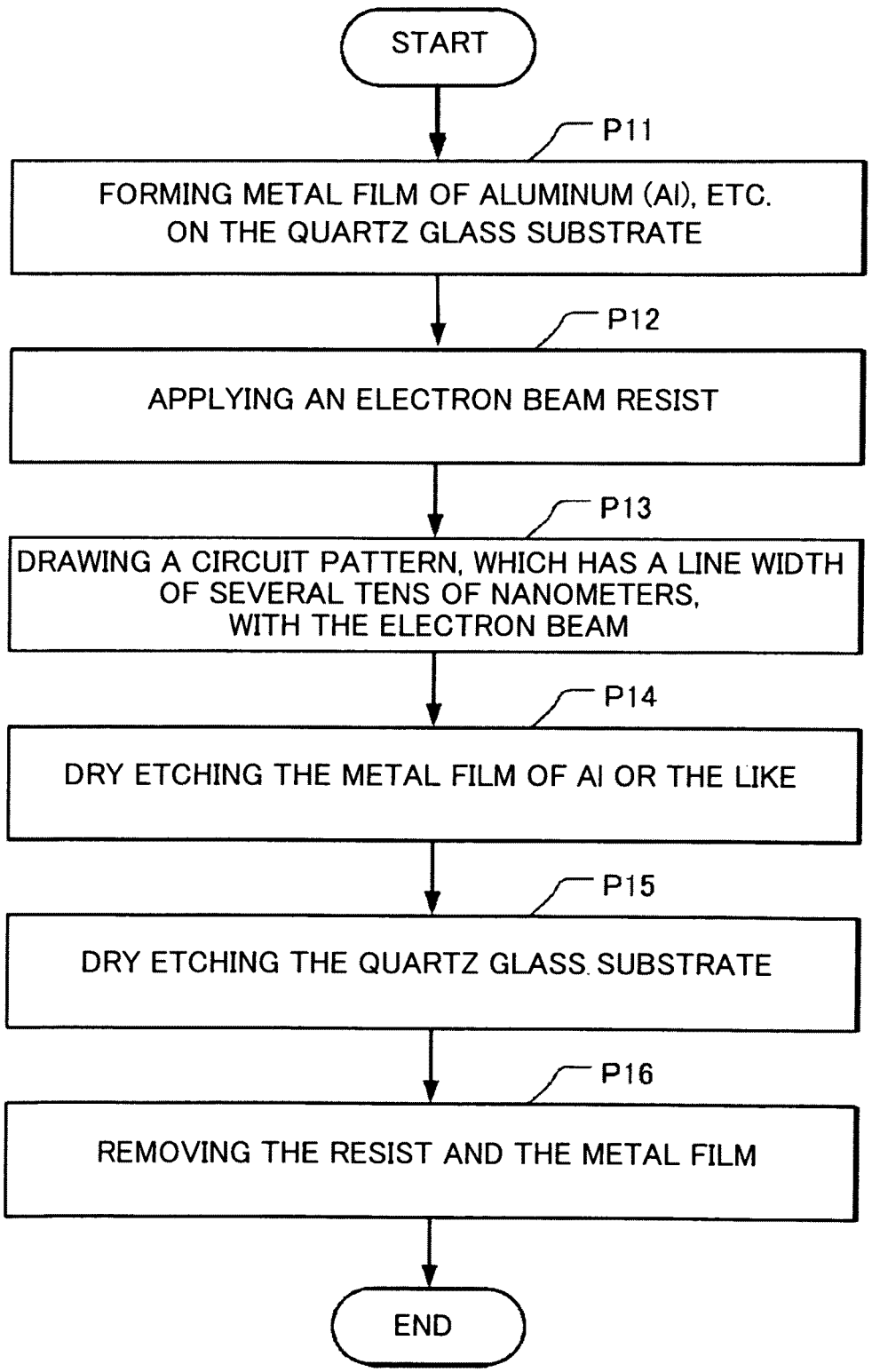
FIG. 3 is a flow chart of a method of producing the master template MTP.

FIG. 3 is a flow chart that depicts a procedure for producing the master template MTP.

In a step P11, a quartz glass substrate with, for example, a size of 25×25 mm and a thickness of 6.35 mm is prepared for becoming the master template MTP. Furthermore, a metal film of aluminum (Al) or the like is formed on the quartz glass substrate by chemical vapor deposition (CVD), sputtering, or the like.

In a step P12, an electron beam resist film is formed on the metal film of the quartz glass substrate.

In a step P13, a circuit pattern with a line width of several tens of nanometers is drawn with the electron beam (not shown) on the resist film of the quartz glass substrate.

In a step P14, the metal film of Al or the like is dry etched with chlorine ($Cl_2$) gas. Furthermore, although it is also possible to form a pattern by wet etching, such a method is not suited to the master template MTP because it produces a cross section that is isotropically etched. Moreover, in dry etching with chlorine ($Cl_2$) gas, the wall surfaces can be fabricated substantially vertically and thereby the circuit pattern drawn with the electron beam is reflected in the metal film.

In a step P15, the quartz glass substrate is dry etched using the metal film of Al or the like as a mask. Methyl fluoride ($CHF_3$) gas, carbon tetrafluoride ($CF_4$) gas, or the like is used as the dry etchant. The depression/protrusion pattern formed by the dry etching on the quartz glass substrate has a depth of between 10 nm and 50 nm.

In a step P16, the residual resist and metal film are removed, and thereby the master template MTP is formed.

<First Method of Producing the Replica Templates RTP>

Figure 4:
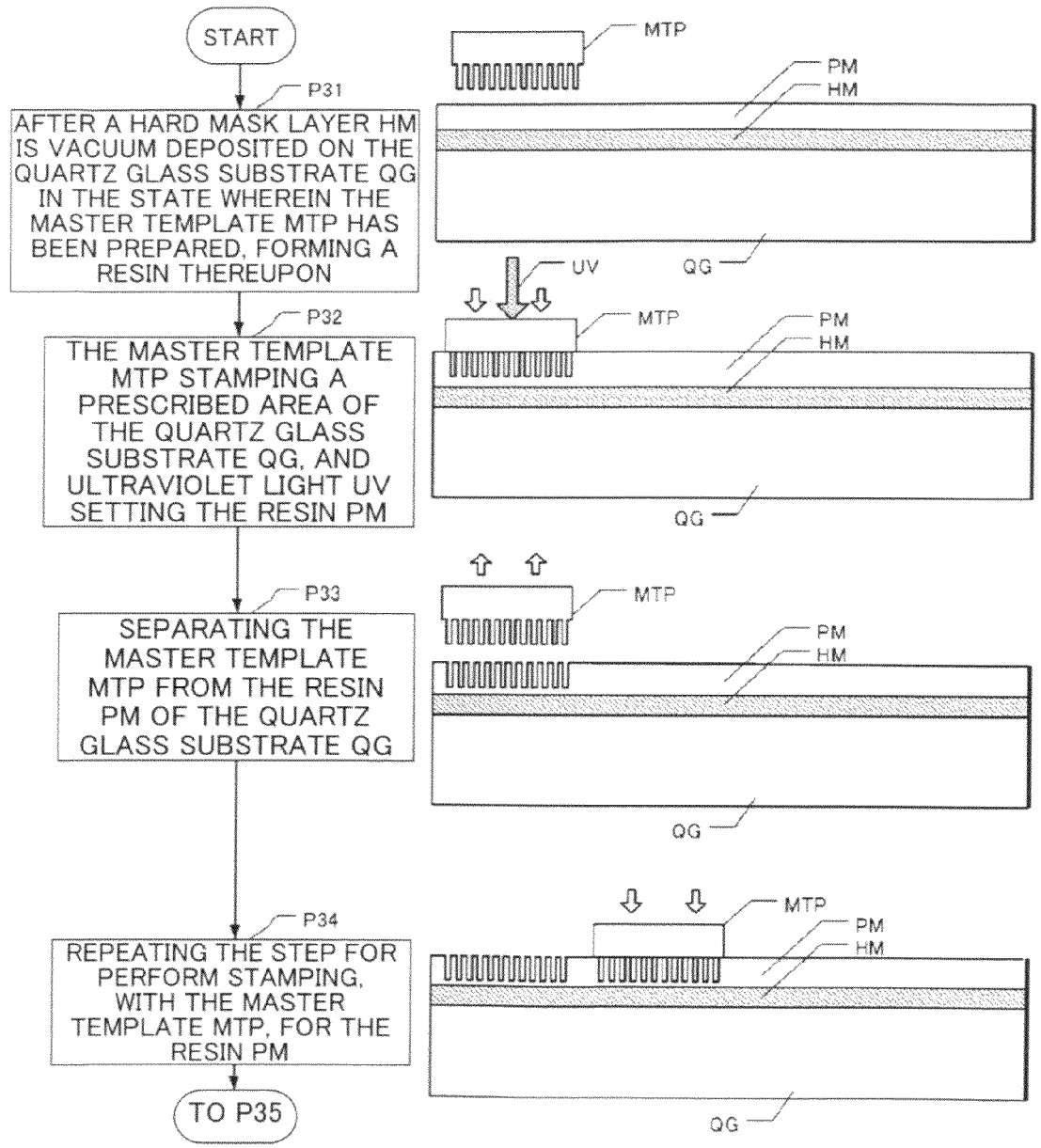
FIG. 4 is a flow chart and a conceptual diagram for explaining a first method of producing the replica templates RTP.
Figure 5:
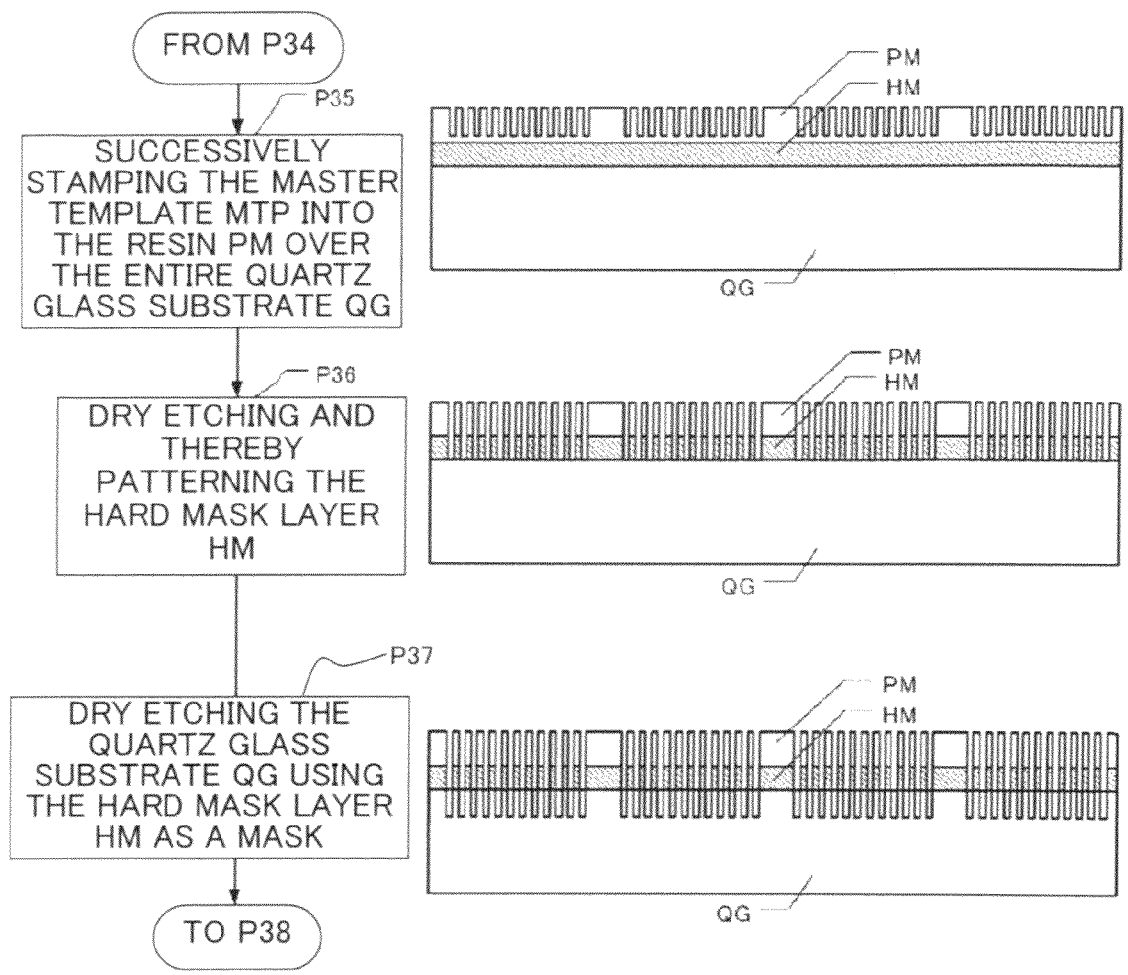
FIG. 5 is a flow chart and a conceptual diagram for explaining the first method of producing the replica templates RTP.
Figure 6:
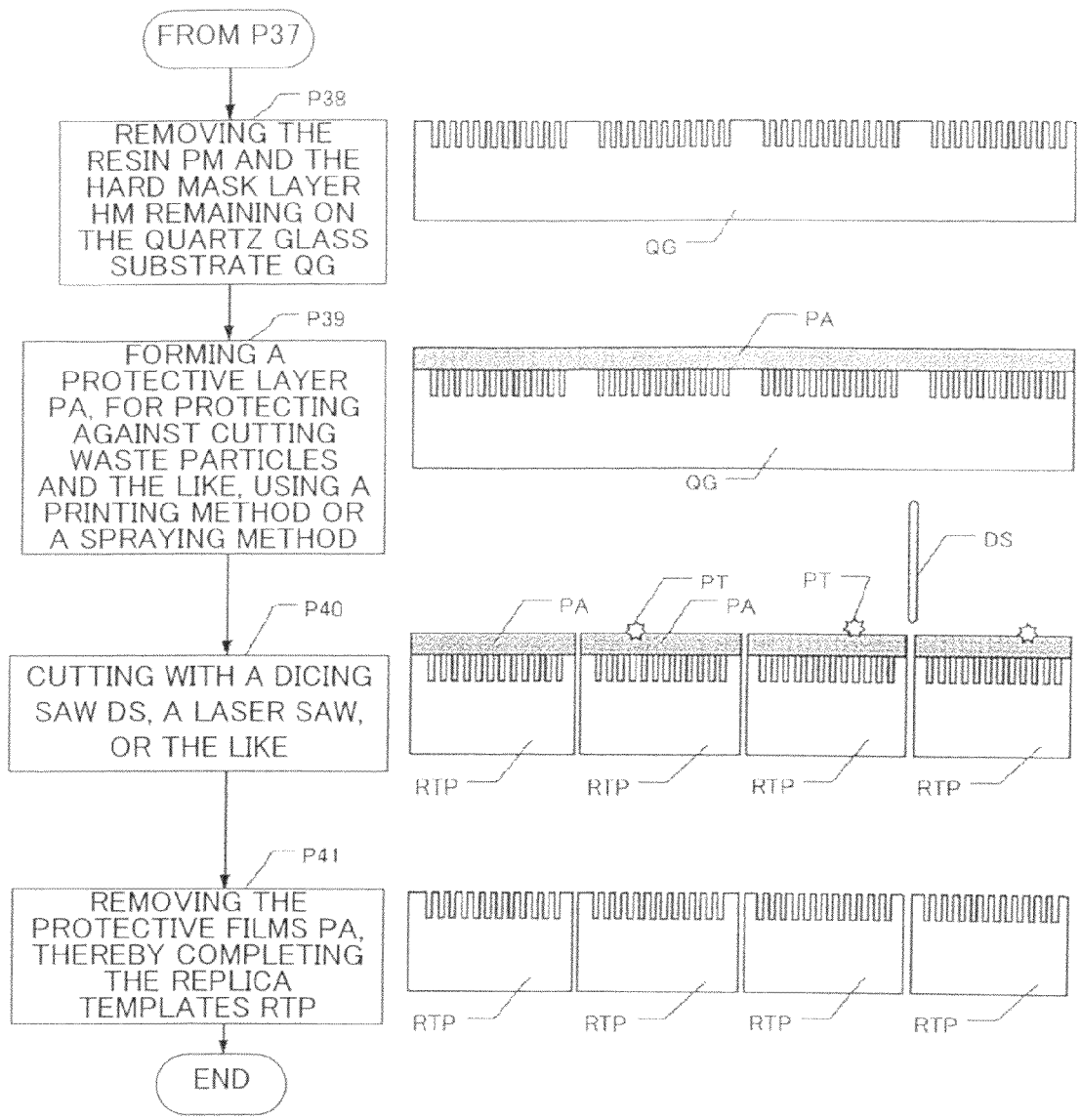
FIG. 6 is a flow chart and a conceptual diagram for explaining the first method of producing the replica templates RTP.

FIG. 4 through FIG. 6 are flow charts of a first method of producing the replica templates RTP using the first nanoimprinting apparatus 200 shown in FIG. 1. In addition, on the right side of each of the steps in the flow chart, a conceptual cross sectional diagram of that step is shown.

In a step P31 of FIG. 4, the master template MTP is prepared. In addition, a hard mask layer HM is formed by vacuum deposition or sputtering on the quartz glass substrate QG, which has a size of, for example, 150×150 mm. As a representative example, a chromium (Cr) layer or an aluminum (Al) layer is used as the hard mask layer HM. The hard mask layer HM is provided to improve corrosion resistance to the etchant when the quartz glass substrate QG is etched. An ultraviolet light setting resin PM is formed on the hard mask layer HM. For example, an acrylic resin, an aliphatic allyl urethane, a nonvolatile material, an aromatic acid methacrylate, an aromatic acrylic acid ester, an acrylated polyester oligomer, an acrylate monomer, a polyethylene glycol dimethacrylate, an aliphatic diacrylate, a trifunctional acid ester, or an epoxy resin is used as the resin PM. In the drawing to the right of the step P31, the resin PM is formed over the entire surface; however, if a low viscosity liquid is used as the resin PM, then the resin PM may be coated only in an area that corresponds to the surface area of the master template MTP.

In a step P32, the pressing elevator EV (refer to FIG. 1) applies pressure such that the master template MTP presses against the ultraviolet light setting resin PM of the quartz glass substrate QG. In so doing, the resin PM in the gap between the master template MTP and the quartz glass substrate QG conforms to the depression/protrusion pattern of the master template MTP. In this state, ultraviolet light UV generated by an ultraviolet light source UVS, which is provided inside the pressing elevator EV, is radiated to the resin PM, and the ultraviolet light UV sets the resin PM.

In a step P33, the master template MTP is separated from the set resin PM. As shown on the right side of the step P33, a depression/protrusion pattern is formed in the set resin PM on the hard mask layer HM of the quartz glass substrate QG. Furthermore, a separable layer is preferably provided on the resin PM beforehand so that the master template MTP can be easily separated from the set resin PM.

In a step P34, the step or operation wherein the XY stage 14 (refer to FIG. 1) moves in the X axial directions or the Y axial directions and the pressing elevator EV stamps the master template MTP into the resin PM is repeated.

In a step P35 of FIG. 5, the master template MTP successively stamps the resin PM over the entire quartz glass substrate QG, as shown in the drawing to the right of the step P35.

In a step P36, the hard mask layer HM is dry etched. In so doing, the front surface of the quartz glass substrate QG is exposed.

In a step P37, the quartz glass substrate QG is dry etched using the hard mask layer HM as a mask. Each of the depression/protrusion patterns formed in the quartz glass substrate QG by the dry etching has a depth of between 10 nm and 100 nm.

In this state, it is possible to inspect for defects during the production of the replica templates RTP by comparing adjacent replica template patterns with one another. When performing this inspection wherein the replica templates RTP are compared, an optical inspection machine can be used. This is because, even if the optical resolution affects the pattern dimensions, it is possible to detect defects whose dimensions are smaller than those of each pixel by comparing the signal strengths of the image sensor's pixels. Although the defect detection sensitivity of an optical inspection machine is lower than that of an inspection machine wherein an electron beam is used, it is advantageous to use the optical inspection machine because of its short inspection time.

In a step P38 of FIG. 6, the resin PM and the hard mask layer HM remaining on the quartz glass substrate QG are removed.

In a step P39, a protective film PA is formed on the quartz glass substrate QG to protect the replica templates RTP from cutting waste particles PT produced during dicing. For example, a macromolecular material such as a jelly-like polyimide resin is used as the protective film PA. In addition, a thermosetting resin material or an ultraviolet light setting resin material may be used as the protective film PA. The protective film PA is applied by a screen printing method or a spraying method that applies resin using a sprayer. In addition, instead of applying a resin, it is also acceptable to affix a protective tape.

In a step P40, the replica templates RTP are produced by cutting the quartz glass substrate QG with a dicing saw DS, a laser saw, or the like. Even if the cutting waste particles PT are generated at this time, defects are not created in the patterns of the replica templates RTP because the replica templates RTP are protected by the protective films PA.

Lastly, in a step P41, the protective films PA are removed from the replica templates RTP, and thereby the plurality of the replica templates RTP is completed. Producing the replica templates RTP in the manner described above makes it possible to improve the mass producibility of the replica templates RTP and, in turn, to improve the manufacture of the semiconductor devices.

<Second Method of Producing the Replica Templates RTP>

Figure 7:
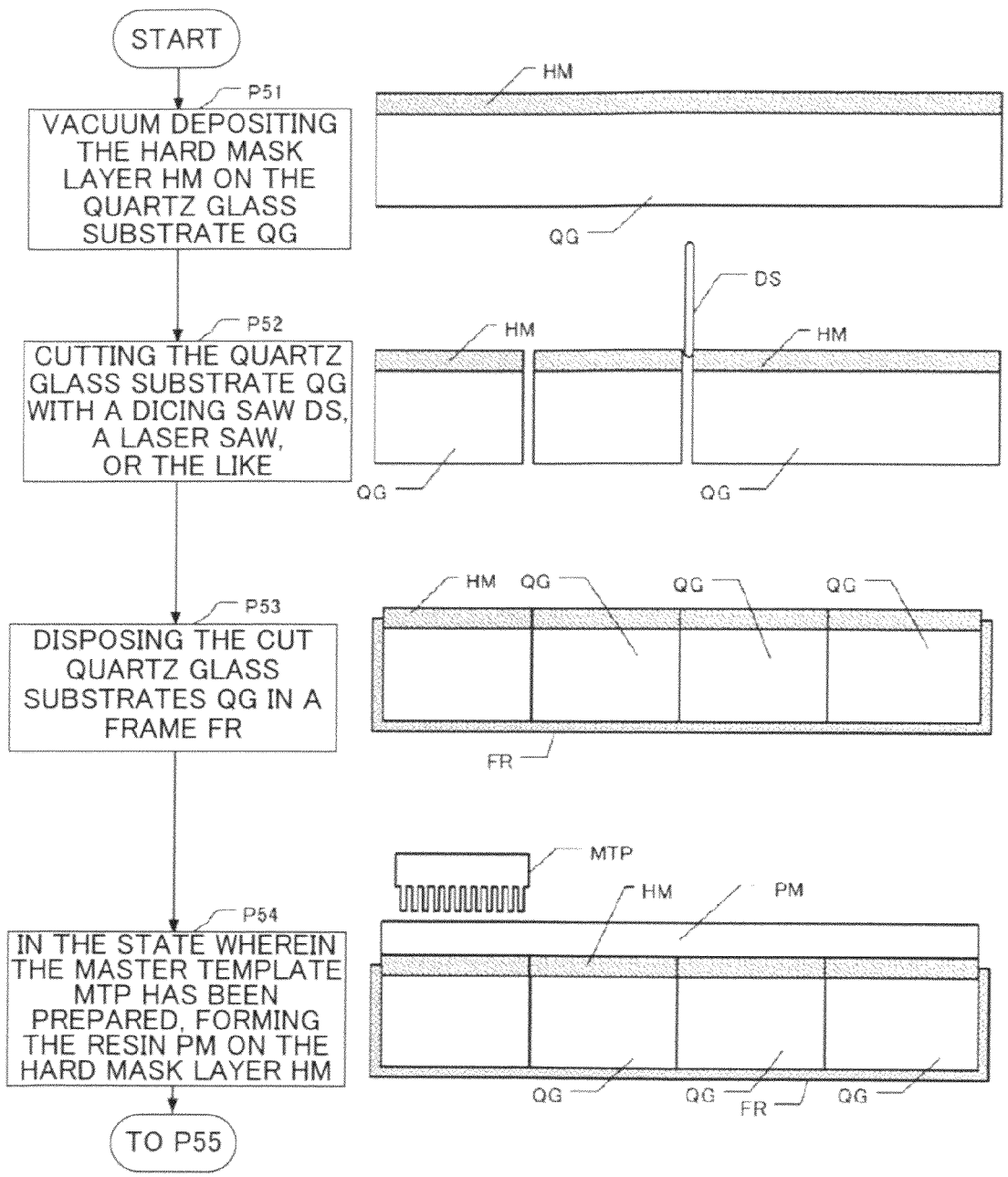
FIG. 7 is a flow chart and a conceptual diagram for explaining a second method of producing the replica templates RTP.
Figure 8:
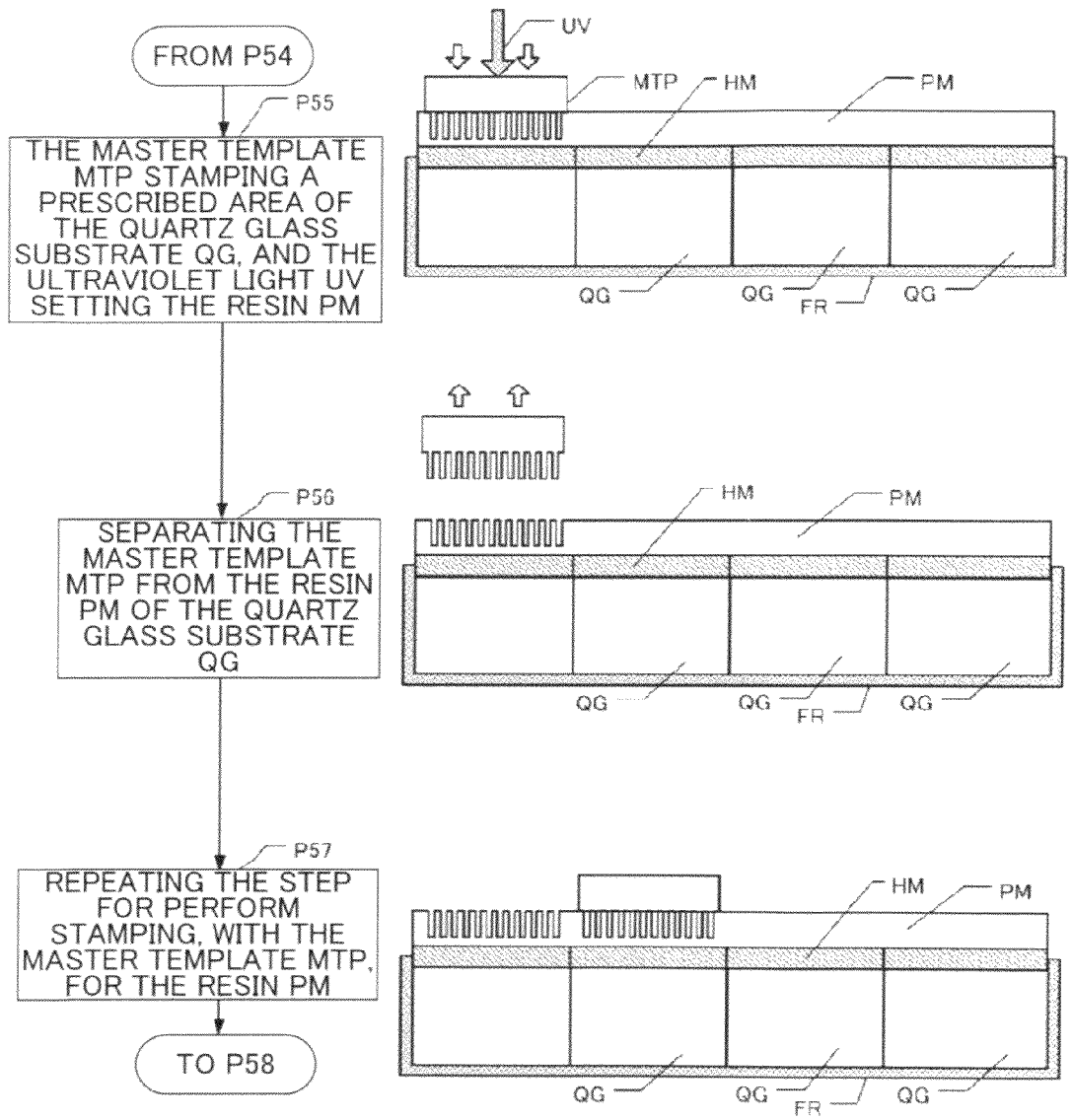
FIG. 8 is a flow chart and a conceptual diagram for explaining the second method of producing the replica templates RTP.
Figure 9:
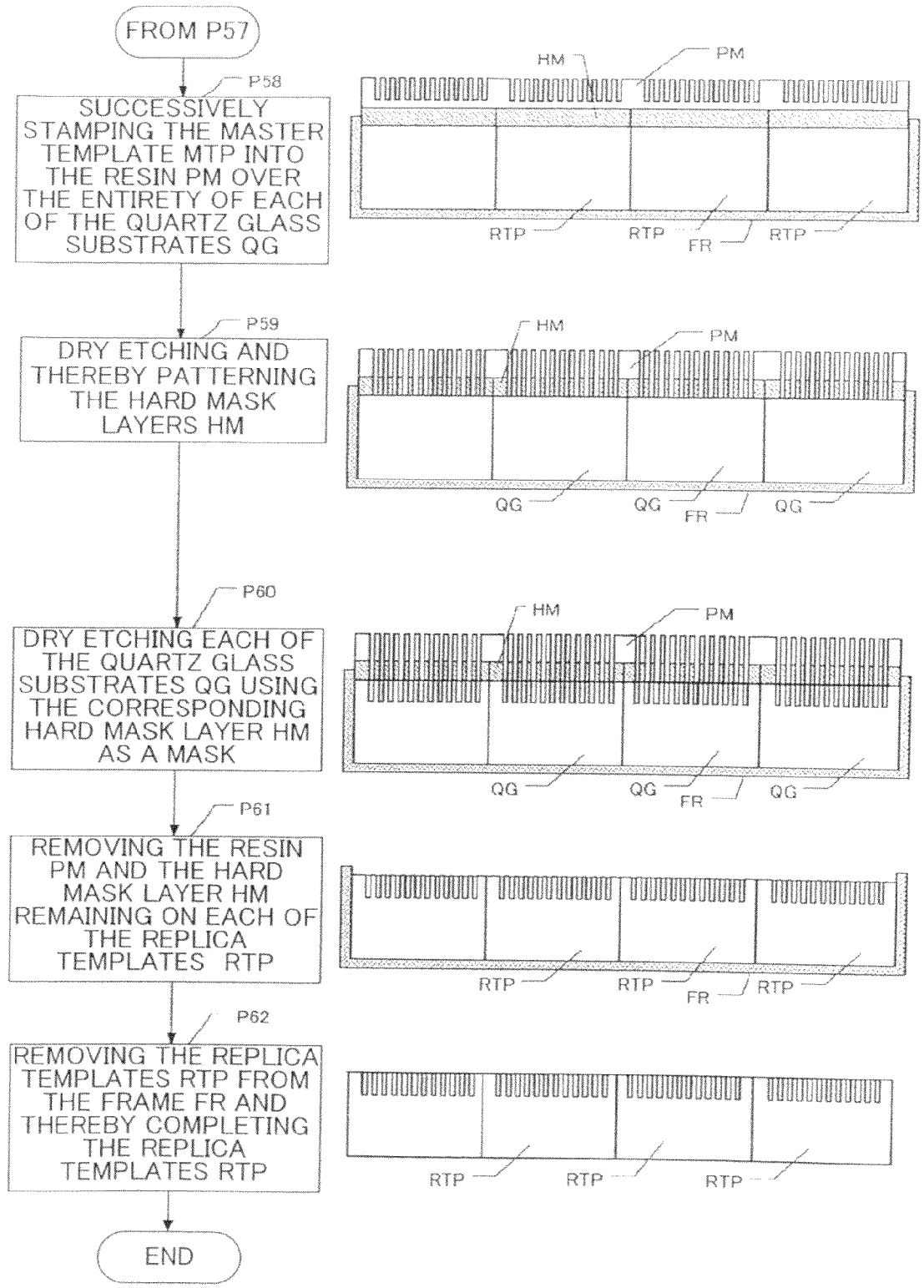
FIG. 9 is a flow chart and a conceptual diagram for explaining the second method of producing the replica templates RTP.

FIG. 7 through FIG. 9 are flow charts of a second method of producing the replica templates RTP using the first nanoimprinting apparatus 200 shown in FIG. 1. In addition, on the right side of each of the steps in the flow chart, conceptual cross sectional diagrams are shown for each of those steps.

In a step P51 in FIG. 7, the hard mask layer HM is formed on the quartz glass substrate QG of, for example, 150×150 mm by vacuum deposition or sputtering.

In a step P52, the quartz glass substrate QG is cut into pieces in the size of, for example, 25×25 mm by the dicing saw DS, a laser saw, or the like. Each of the cut quartz glass substrates QG is cleaned, and any of the cutting waste particles PT produced during the dicing is removed. Thereby, a plurality of the quartz glass substrates QG is prepared. Furthermore, if quartz glass pieces of 25×25 mm in size are prepared from the start, then the step P52 is not necessary.

In a step P53, the plurality of the cleaned quartz glass substrates QG is disposed in a row in a frame FR. Subsequently, the plurality of the quartz glass substrates QG contained in the frame FR can be treated as equivalent to a single one of the quartz glass substrates QG.

In a step P54, the master template MTP is prepared. In addition, the ultraviolet light setting resin PM is formed on the hard mask layer HM. In the drawing to the right of the step P54, the resin PM is formed over the entire surface; however, if a low viscosity liquid is used as the resin PM, then just the area corresponding to the surface area of the master template MTP may be coated.

In a step P55 in FIG. 8, the pressing elevator EV (refer to FIG. 1) applies pressure such that the master template MTP is pressed against the ultraviolet light setting resin PM on the quartz glass substrate QG. In so doing, the resin PM in the gap between the master template MTP and the quartz glass substrate QG conforms to the depression/protrusion pattern of the master template MTP. In this state, the resin PM is set by radiating ultraviolet light UV, which is generated by the ultraviolet light source UVS, to the resin PM.

In a step P56, the master template MTP is separated from the set resin PM. As shown on the right side of the step P56, the depression/protrusion pattern is formed in the set resin PM on the hard mask layer HM of the quartz glass substrate QG. Furthermore, a separable layer may be provided on the resin PM beforehand so that the master template MTP can be easily separated from the set resin PM.

In a step P57, the operation or step wherein the XY stage 14 (refer to FIG. 1) moves in the X axial directions and the Y axial directions and the pressing elevator EV stamps the master template MTP into the resin PM is repeated.

As shown in the drawing to the right of a step P58 in FIG. 9, the master template MTP stamps the resin PM over the entirety of each of the quartz glass substrates QG.

In a step P59, the hard mask layers HM are dry etched. In so doing, the front surface of each of the quartz glass substrates QG is exposed.

In a step P60, each of the quartz glass substrates QG is dry etched using the corresponding hard mask layer HM as a mask. The depression/protrusion pattern formed by the dry etching in each of the quartz glass pieces QG has a depth of between 10 nm and 100 nm.

In this state, it is possible to inspect for defects during the production of the replica templates RTP by comparing the patterns of adjacent replica templates RTP with each other.

In a step P61, the resin PM and the hard mask layer HM remaining on each of the replica templates RTP are removed.

Lastly, in a step P62, the replica templates RTP are removed from the frame FR. Producing the replica templates RTP in the manner described above makes it possible to improve the mass producibility of the replica templates RTP and, in turn, to improve semiconductor device productivity.

In addition, the embodiment recited above explains the case wherein an ultraviolet light setting resin is used as the setting resin PM, but a thermosetting resin may be used. In addition, quartz glass is used for the base material of each of the replica templates RTP, but some other glass may be used. Furthermore, if an ultraviolet light setting resin is used as the resin PM, then the base material should be one wherethrough the ultraviolet light can transmit.

<Third Method of Producing the Replica Templates RTP>

Figure 10:
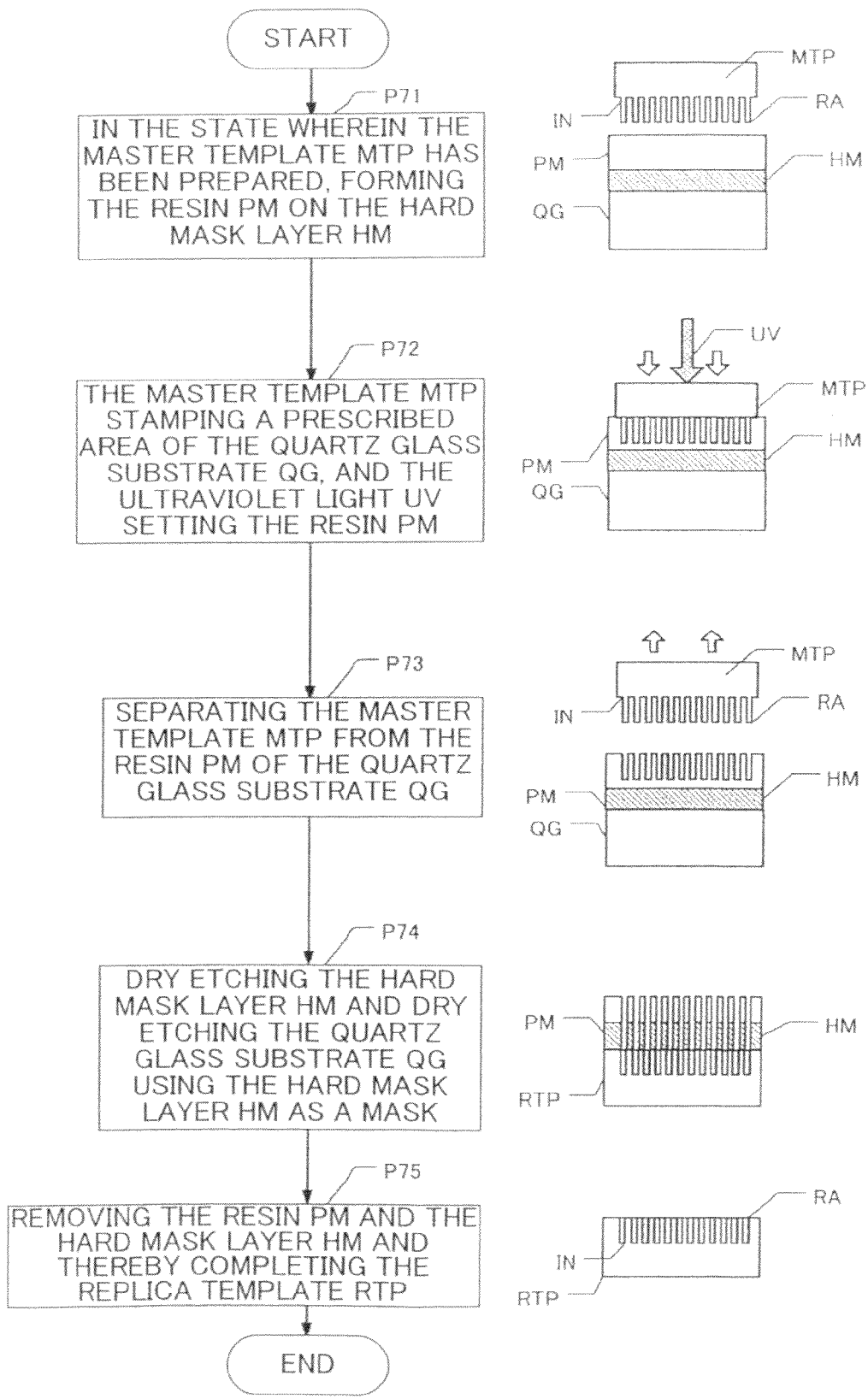
FIG. 10 is a flow chart of a method of producing the replica templates RTP.

FIG. 10 is a flow chart that depicts a method of producing the replica templates RTP one by one rather than all at once. In addition, on the right side of each block of the flow chart, a conceptual cross sectional diagram for the corresponding step is shown.

In a step P71, one of the master templates MTP (hereinbelow, called "master template"), which are manufactured by an electron beam based on design data one datum at a time, is prepared. A depression/protrusion pattern is formed in the master template MTP and comprises the protruding areas RA and the depressed areas IN. The master template MTP is inspected using an electron beam inspection apparatus, an electron microscope, or the like. In addition, the quartz glass substrate QG, which comprises the hard mask layer HM formed by vacuum deposition or sputtering, is prepared. The ultraviolet light setting resin PM is formed on the hard mask layer HM. The resin PM is a low viscosity liquid.

In a step P72, the master template MTP stamps the ultraviolet light setting resin PM of the quartz glass substrate QG. In so doing, the resin PM in the gap between the master template MTP and the quartz glass substrate QG conforms to the protrusion/depression pattern of the master template MTP. In this state, the resin PM is set by radiating the ultraviolet light UV to the resin PM. Furthermore, for example, an acrylic resin is used as the resin PM.

In a step P73, the master template MTP is separated from the set resin PM. As shown on the right side of this step, the depression/protrusion pattern is formed in the set resin PM on the hard mask layer HM of the quartz glass substrate QG. Furthermore, the resin PM is not limited to an ultraviolet light setting resin and may be a thermosetting resin.

In a step P74, the hard mask layer HM is dry etched. In so doing, the front surface of the quartz glass substrate QG is exposed. Furthermore, the quartz glass substrate QG is dry etched using the hard mask layer HM as a mask, and thereby the depression/protrusion pattern of the replica template RTP is formed.

In a step P75, the resin PM and the hard mask layer HM remaining on the replica template RTP are removed, and thereby the replica template RTP is completed. The depression/protrusion pattern of the replica template RTP also has the protruding areas RA and the depressed areas IN. Furthermore, in FIG. 10, the depression/protrusion pattern is illustrated in an exaggerated manner; in actuality, the depression/protrusion pattern is a line-and-space pattern of, for example, 10-50 nm with a depression/protrusion height of, for example, between 10 nm and 100 nm.

<Structure of a First Replica Template Inspection Apparatus 100>

Figure 11:
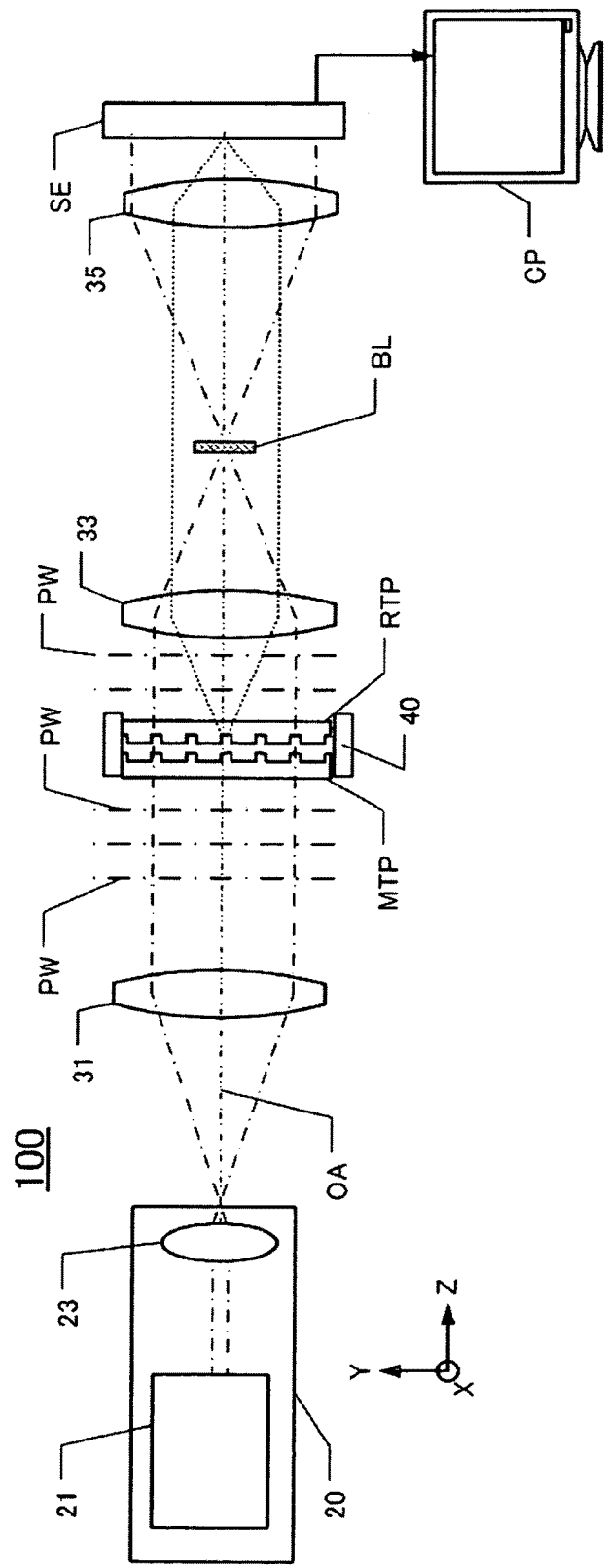
FIG. 11 is a block schematic diagram of a first replica template inspection apparatus 100.

FIG. 11 is a block schematic diagram of a first replica template inspection apparatus 100.

As shown in FIG. 11, the first replica template inspection apparatus 100 comprises an inspection light source part 20, a collimator lens 31, a condenser lens 33, a light shielding block BL, an image forming lens 35, and a two dimensional photosensor SE.

The inspection light source part 20 comprises a solid state laser 21, which emits laser light with a wavelength of, for example, 193 nm, and a condenser lens 23. For example, the solid state laser 21 emits parallel light with a diameter of φ3 on the Krumbein phi scale, and the condenser lens 23 converges the laser light to form a point light source. The laser light that emerges from the condenser lens 23 proceeds to the collimator lens 31.

The collimator lens 31 changes the laser light to a parallel light beam. The wavefronts of the parallel light beam are plane waves PW. The master template MTP and the replica templates RTP explained referencing FIG. 4 through FIG. 10 are disposed on a stage 40 within these plane waves PW. The stage 40 is disposed such that the depression/protrusion pattern surface of the master template MTP and the depression/protrusion pattern surface of one of the replica templates RTP face one another (i.e., such that a depressed part of one faces a protruding part of the other). In addition, the surfaces of the master template MTP and the replica template RTP are disposed such that they are parallel to the wavefronts of the plane waves PW, in other words, such that they are perpendicular to an optical axis OA. Furthermore, instead of disposing the master template MTP on the inspection light source part 20 side as shown in FIG. 11, the replica template RTP may be disposed on the inspection light source part 20 side.

The light beam that passes through the master template MTP and the replica template RTP proceeds to the condenser lens 33 and the image forming lens 35. The light shielding block BL, which has a prescribed diameter, is disposed along the optical axis OA and in the vicinity of the pupil position of the optical system that comprises the condenser lens 33 and the image forming lens 35 (i.e., the rear side focal plane, namely, the Fourier transform plane, of the condenser lens 33).

Figure 22:
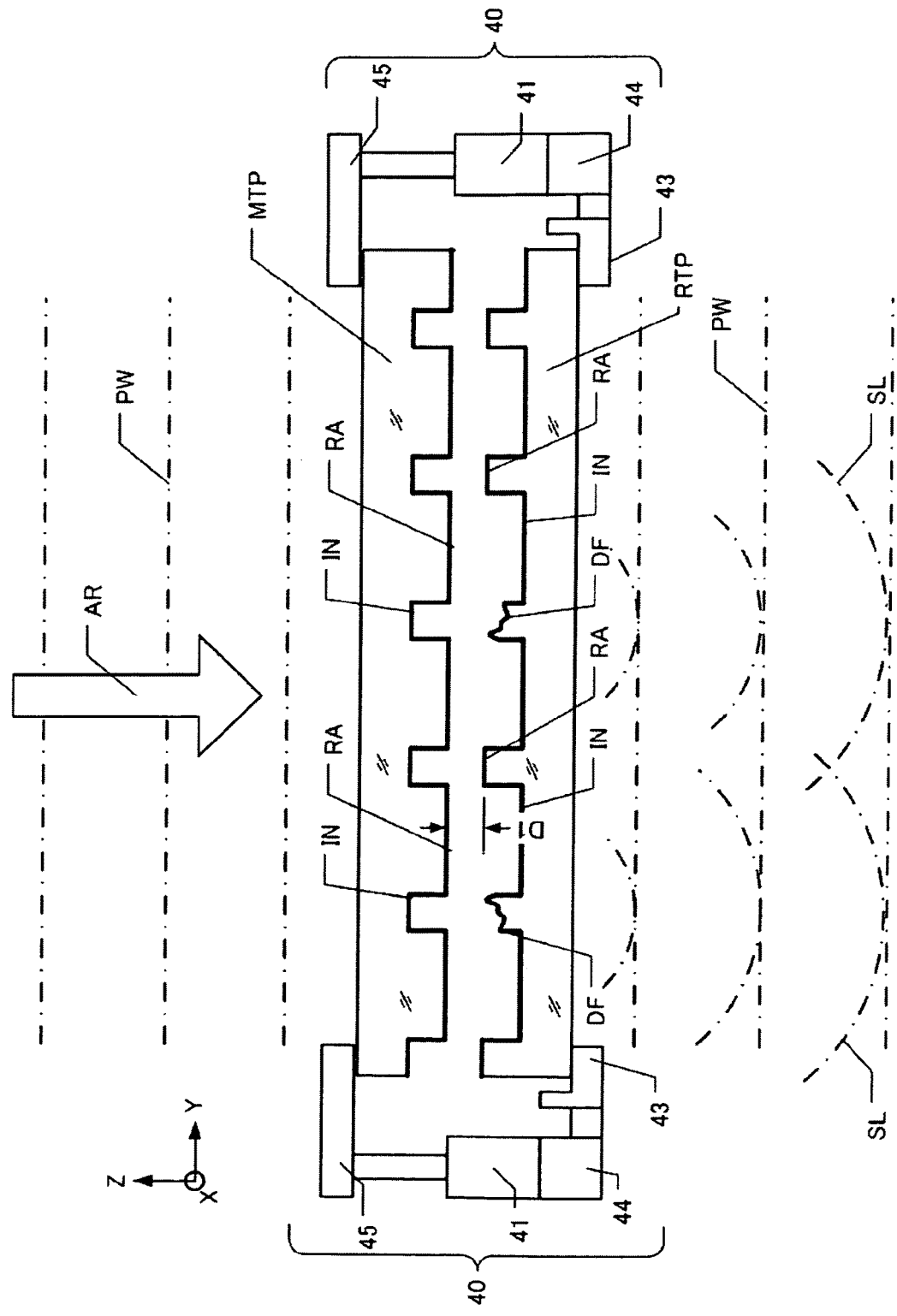
FIG. 22 is an enlarged cross sectional view of the stage 40 of the master template MTP and the replica templates RTP for the particular case wherein the replica templates RTP have defects DF.

If defects DF are present in the replica template RTP, then the plane waves PW will be modulated, generating scattered lights SL of spherical waves and the like (refer to FIG. 22). If the defects DF are not present in the replica template RTP, then the plane waves PW will not be modulated and will remain as plane waves. The light shielding block BL blocks the plane waves PW that transmit through the replica template RTP but does not block the scattered lights SL, which therefore reach the two dimensional photosensor SE. In other words, if there are defective locations in the replica template RTP, then the scattered lights SL of those defective locations will be detected by the two dimensional photosensor SE. If no defects DF whatsoever are present in the replica template RTP, then the two dimensional photosensor SE will receive no light. In other words, the portions with none of the defects DF are dark, and the defects DF appear as point light sources and thereby are detected.

The two dimensional photosensor SE is, for example, a two dimensional CCD, and the output from the two dimensional photosensor SE is supplied to a computer CP. The computer CP displays the defective locations of the replica template RTP based on the magnification of the optical system and the output from the two dimensional photosensor SE.

Furthermore, it is also effective if the first replica template inspection apparatus 100 not only inspects the replica template RTP for the defects DF but also for the presence of the waste particles PT such as dust. If the waste particles PT are present between the master template MTP and the replica template RTP, then the scattered lights SL are generated. Consequently, the computer CP can display the locations and the sizes of the waste particles PT based on the magnification of the optical system and the output from the two dimensional photosensor SE.

<Structure of Second Replica Template Inspection Apparatus 110>

Figure 12:
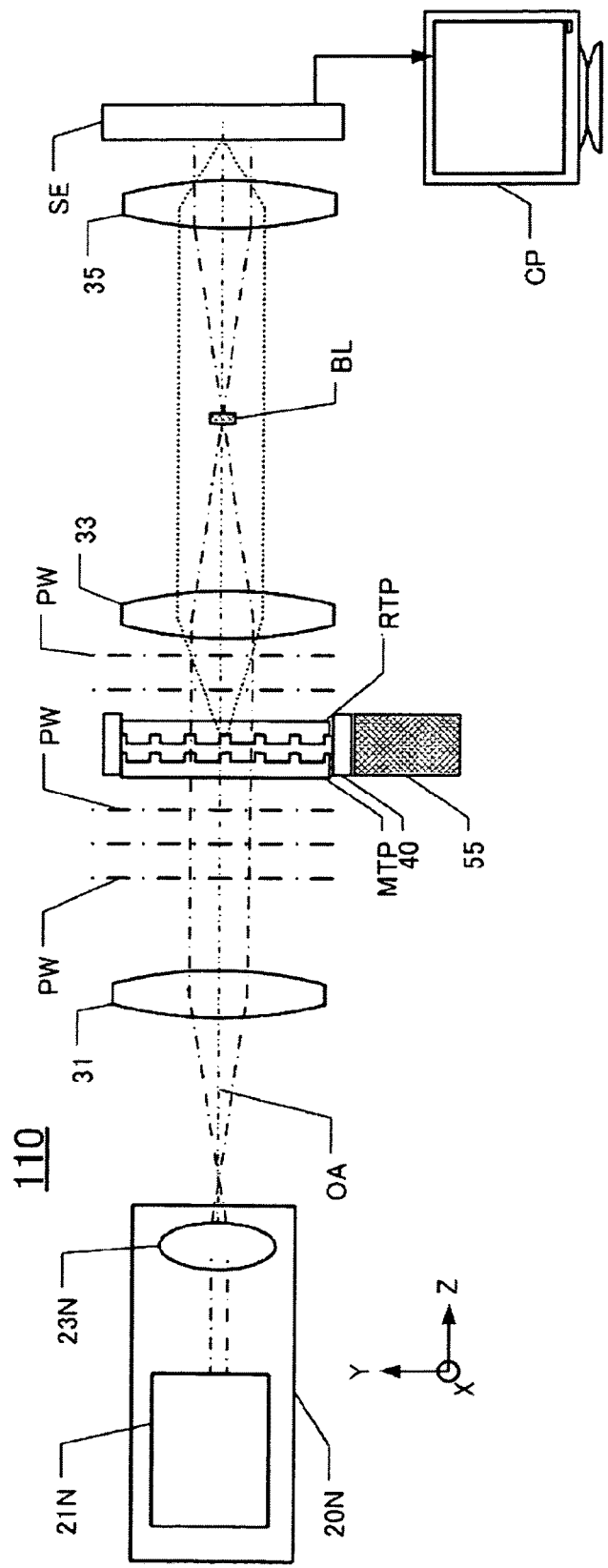
FIG. 12 is a block schematic diagram of a second replica template inspection apparatus 110.

FIG. 12 is a block schematic diagram of a second replica template inspection apparatus 110.

In the first replica template inspection apparatus 100, the laser light is radiated over the entire surfaces of the master template MTP and the replica template RTP. In the second replica template inspection apparatus 110, the laser light is radiated to part of the surfaces of the master template MTP and the replica template RTP. Constituent elements that are identical to those in the first replica template inspection apparatus 100 are assigned the same symbols.

As shown in FIG. 12, the second replica template inspection apparatus 110 comprises an inspection light source part 20N, the collimator lens 31, the condenser lens 33, the light shielding block BL, the image forming lens 35, and the two dimensional photosensor SE.

The inspection light source part 20N comprises a solid state laser 21N, which, emits laser light with a wavelength of, for example, 193 nm, and a second condenser lens 23N. The solid state laser 21N emits parallel light with a diameter of approximately ϕ2, and the second condenser lens 23N converges the laser light, thereby forming a point light source. The laser light emitted from the second condenser lens 23N is a light beam with a diameter of approximately several millimeters. Furthermore, the laser light, whose diameter is approximately several millimeters, proceeds to the collimator lens 31.

The stage 40, whereon the master template MTP and the replica template RTP are disposed, is mounted on a movable table 55. The movable table 55 has a long stroke and can move a distance of, for example, approximately 25 mm in the X axial directions and approximately 25 mm in the Y axial directions.

The operation will now be explained simply. In the second replica template inspection apparatus 110, the inspection light source part 20N has a small radiating area. Consequently, by virtue of the movable table 55 moving the stage 40 great distances in the X axial directions and the Y axial directions, the master template MTP and the replica template RTP are irradiated with the laser light over their entire surfaces.

In addition, although the movable table 55 is provided to the stage 40, the movable table 55 may be provided to the inspection light source part 20N. Namely, the inspection light and the template should be able to be scanned relative to one another. Furthermore, the movable table 55 does not necessarily have to be prepared as long as the stage 40 can move in, for example, nanometer units by approximately 25 mm in the X axial directions and approximately 25 mm in the Y axial directions.

<Structure of Third Replica Template Inspection Apparatus 120>

Figure 13:
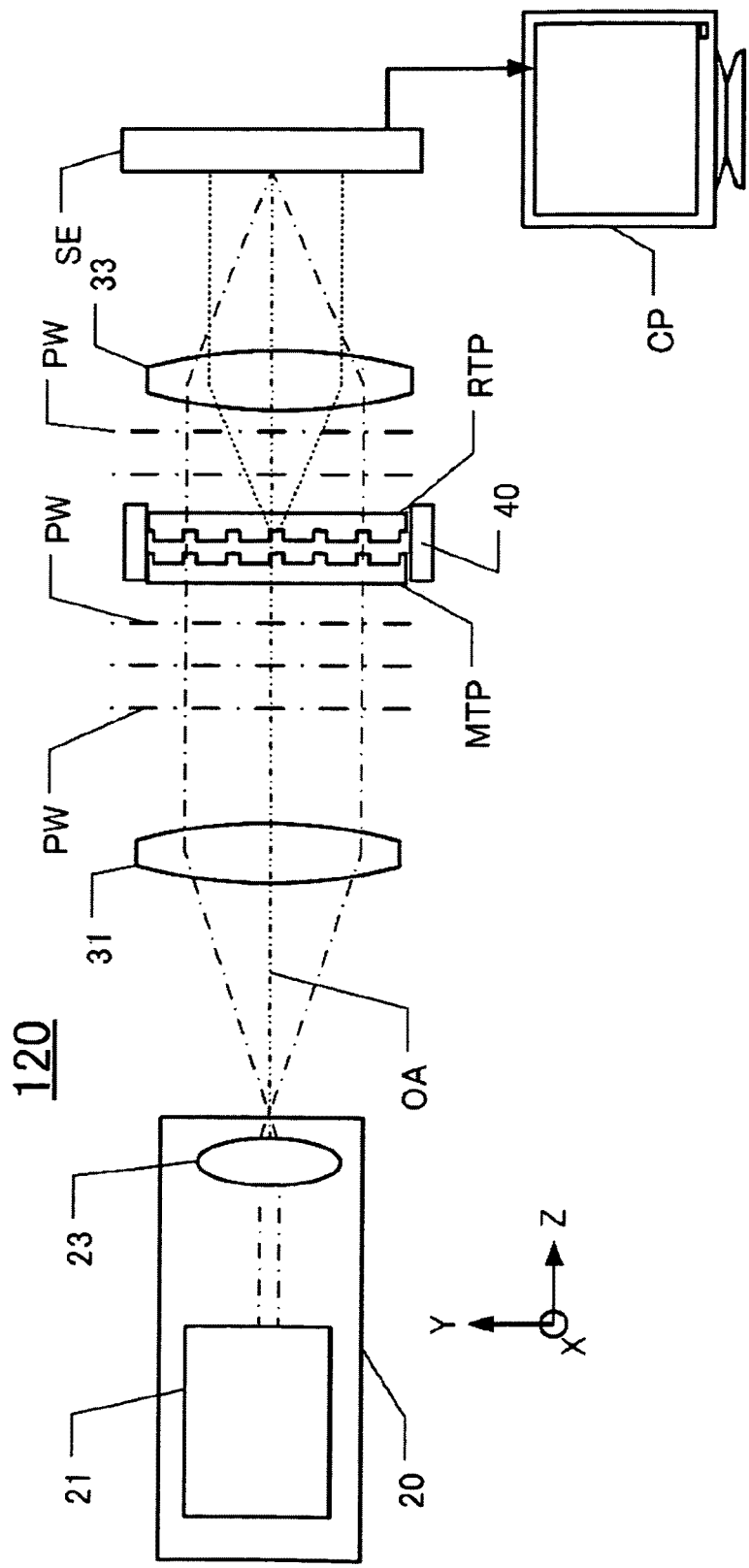
FIG. 13 is a block schematic diagram of a third replica template inspection apparatus 120.

FIG. 13 is a block schematic diagram of a third replica template inspection apparatus 120.

In the first replica template inspection apparatus 100, the scattered lights SL, the images of which are formed by the image forming lens 35, are observed by the two dimensional photosensor SE. However, in the third replica template inspection apparatus 120, the light intensity distribution is observed at the pupil position (i.e., at the rear side focal plane, namely, the Fourier transform plane, of the condenser lens 33). Constituent elements identical to those in the first replica template inspection apparatus 100 are assigned the same symbol.

As shown in FIG. 13, the third replica template inspection apparatus 120 comprises the inspection light source part 20, the collimator lens 31, the condenser lens 33, and the two dimensional photosensor SE. Although the first replica template inspection apparatus 100 comprises the light shielding block BL and the image forming lens 35, the third replica template inspection apparatus 120 does not.

The two dimensional photosensor SE receives the laser light, which has a given light intensity distribution, and observes the effective far field pattern. If none of the defects DF are present in the replica template RTP, then the plane waves PW are not modulated and remain as plane waves. First, the light intensity distribution of the plane waves PW is output from the two dimensional photosensor SE and supplied to the computer CP. The computer CP stores the light intensity distribution. If the defects DF are present in the replica template RTP, then the plane waves PW are modulated and the scattered lights SL of spherical waves and the like are generated; furthermore, the light intensity distributions of both the plane waves PW and the scattered lights SL are output from the two dimensional photosensor SE and supplied to the computer CP. The computer CP stores the light intensity distributions. The computer CP detects any defective locations of the replica template RTP by comparing the light intensity distribution of the plane waves PW alone with the light intensity distributions of both the plane waves PW and the scattered lights SL.

If the area of the replica template RTP irradiated by the laser light is small as in the second replica template inspection apparatus 110 explained referencing FIG. 12, then the movable table 55 may be adapted to the third replica template inspection apparatus 120. The third replica template inspection apparatus 120 is particularly suited to the detection of the waste particles PT.

<Structure of Fourth Replica Template Inspection Apparatus 130>

Figure 14:
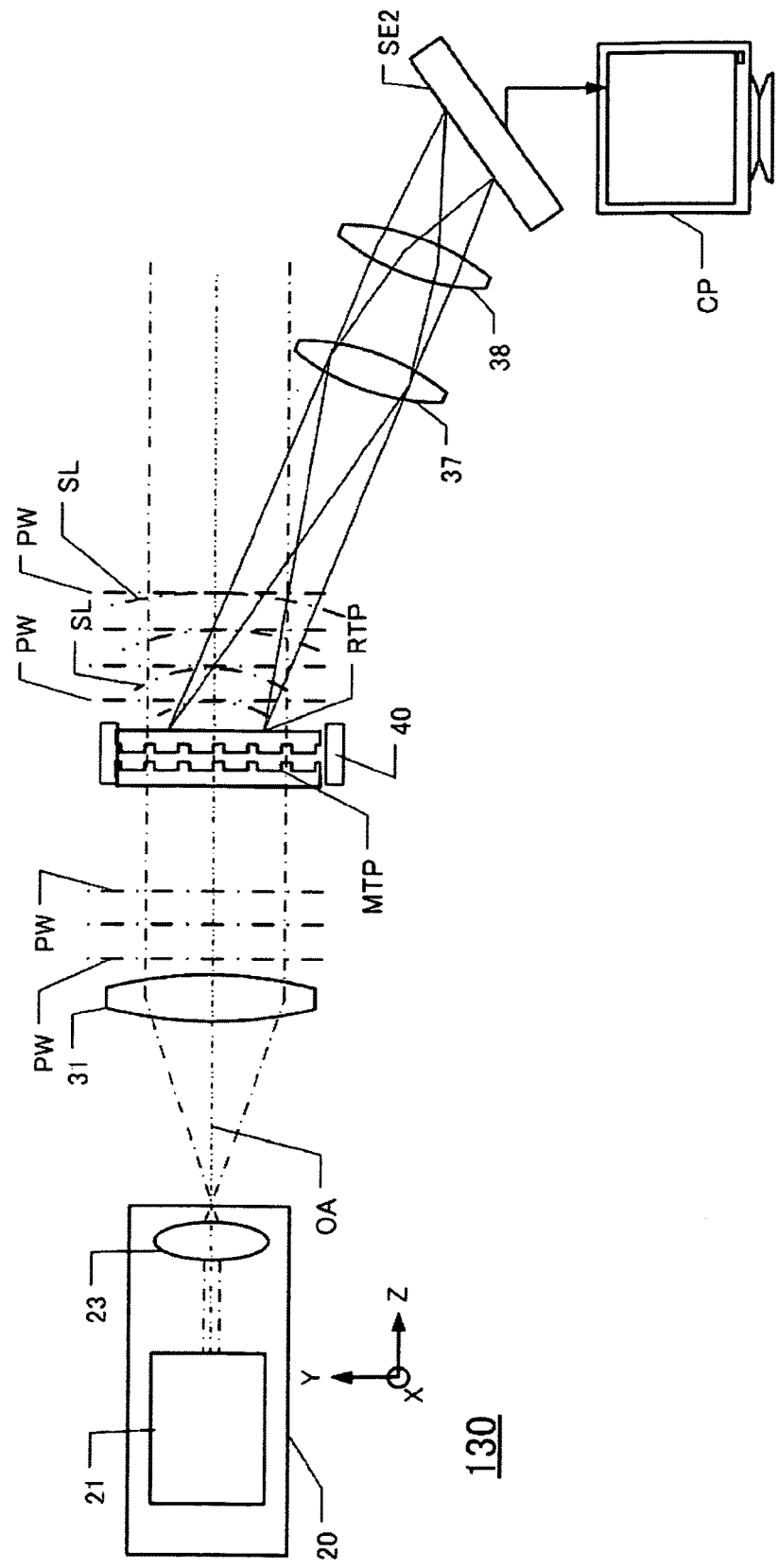
FIG. 14 is a block schematic diagram of a fourth replica template inspection apparatus 130.

FIG. 14 is a block schematic diagram of a fourth replica template inspection apparatus 130. Members identical to those in the first replica template inspection apparatus 100 shown in FIG. 11 are assigned the same symbols.

As shown in FIG. 14, the fourth replica template inspection apparatus. 130 comprises the inspection light source part 20, the collimator lens 31, a second condenser lens 37, a second image forming lens 38, and a second two dimensional photosensor SE2.

Unlike the first replica template inspection apparatus 100 shown in FIG. 11, in the fourth replica template inspection apparatus 130 shown in FIG. 14, the second condenser lens 37 and the second image forming lens 38 are not disposed along the optical axis OA but rather are tilted with respect to the optical axis OA. In addition, the light shielding block BL is not provided. Furthermore, the second two dimensional photosensor SE2 is not disposed along the optical axis OA. In addition, the second two dimensional photosensor SE2 is disposed tilted with respect to the optical axis OA such that an image forming relationship is satisfied in the shifting and tilting of the second condenser lens 37 and the second image forming lens 38 with respect to the master template MTP and the replica template RTP.

If the defects DF are present in the replica template RTP, then the plane waves PW are modulated, which generates the scattered lights SL of spherical waves and the like. The plane waves PW proceed in one of the directions of the optical axis OA that connects the inspection light source part 20 and the collimator lens 31, while the scattered lights SL proceed both in and outside of that direction. Consequently, some of each of the scattered lights SL proceeds to the optical system that comprises the second condenser lens 37 and the second image forming lens 38 and are then condensed onto the second two dimensional photosensor SE2, thereby forming an image of the defects DF of the replica template RTP. The light of the plane waves PW does not enter this optical system, and consequently the light shielding block BL shown in FIG. 11 may be eliminated. Thus, if the defects DF are present in the replica template RTP, then the scattered lights SL produced thereby are detected by the second two dimensional photosensor SE2. If none of the defects DF are present in the replica template RTP, then the second two dimensional photosensor SE2 does not detect any light and the light received signal is not output.

<Structure of Fifth Replica Template Inspection Apparatus 140>

Figure 15:
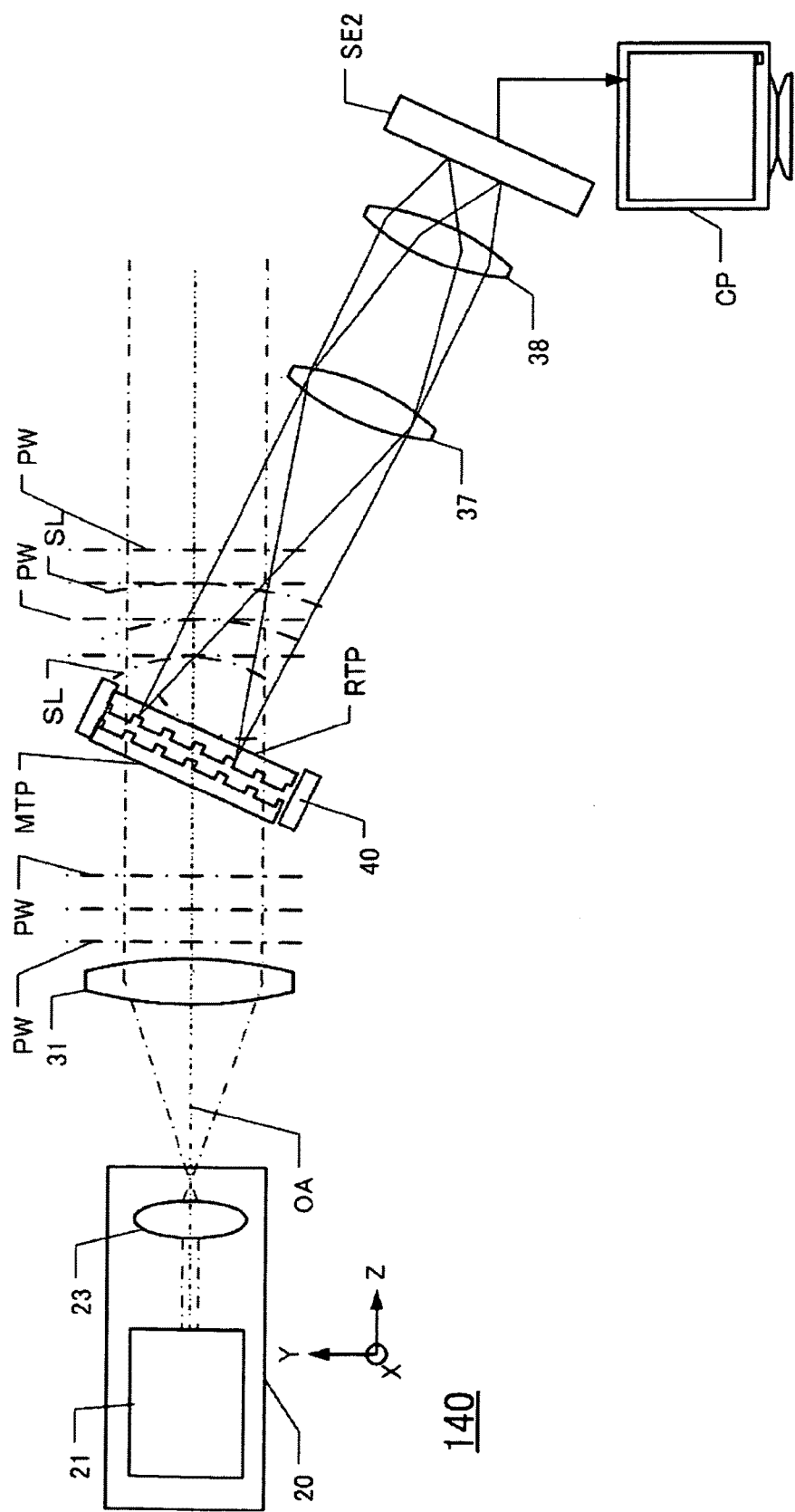
FIG. 15 is a block schematic diagram of a fifth replica template inspection apparatus 140.

FIG. 15 is a block schematic diagram of a fifth replica template inspection apparatus 140. Members identical to those in the first replica template inspection apparatus 100 shown in FIG. 11 are assigned the same symbols.

As shown in FIG. 15, the fifth replica template inspection apparatus 140 comprises the inspection light source part 20, the collimator lens 31, the second condenser lens 37, the second image forming lens 38, and the second two dimensional photosensor SE2.

Unlike the first replica template inspection apparatus 100 shown in FIG. 11, in the fifth replica template inspection apparatus 140 shown in FIG. 15, the stage 40, the second condenser lens 37, the second image forming lens 38, and the second two dimensional photosensor SE2 are not disposed along the optical axis OA. Furthermore, these members are disposed tilted at the same angle with respect to the optical axis OA. In addition, the light shielding block BL is not provided.

Even if the plane waves PW enter the tilted master template MTP and the tilted replica template RTP, the plane waves PW emerge as plane waves from the master template MTP and the replica template RTP.

If the defects DF are present in the replica template RTP, then the scattered lights SL are generated. The plane waves PW proceed in one of the directions of the optical axis OA that connects the inspection light source part 20 and the collimator lens 31, while the scattered lights SL proceed both in and outside of that direction. Consequently, some of each of the scattered lights SL proceeds to the optical system that comprises the second condenser lens 37 and the second image forming lens 38 and are then condensed on the second two dimensional photosensor SE2, thereby forming an image of the defects DF of the replica template RTP. Because the light of the plane waves PW does not enter this optical system, the lightshielding block BL shown in FIG. 11 may be eliminated.

<Structure of Sixth Replica Template Inspection Apparatus 150>

Figure 16:
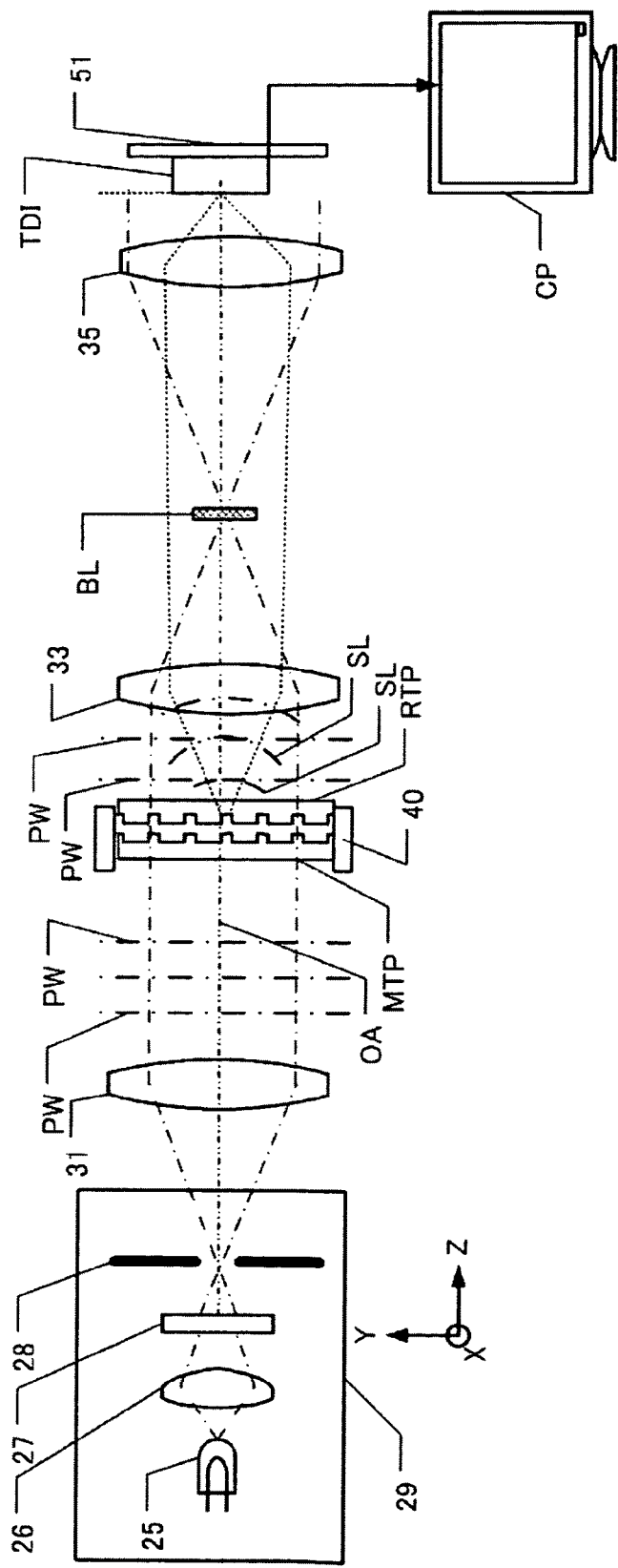
FIG. 16 is a block schematic diagram of a sixth replica template inspection apparatus 150.

FIG. 16 is a block schematic diagram of a sixth replica template inspection apparatus 150. Members identical to those in the first replica template inspection apparatus 100 shown in FIG. 11 are assigned the same symbols.

As shown in FIG. 16, the sixth replica template inspection apparatus 150 comprises an inspection light source part 29, the collimator lens 31, the condenser lens 33, the image forming lens 35, and a time delay and integrating sensor TDI.

The sixth replica template inspection apparatus 150 shown in FIG. 16 differs from the first replica template inspection apparatus 100 shown in FIG. 11 in that the inspection light source part 29 and the time delay and integrating sensor TDI are provided.

The inspection light source part 29 comprises: a short wavelength lamp 25, which emits broad spectrum light in the range of, for example, 150-400 nm; a condenser lens 26; a wavelength selection filter 27; and a pinhole plate 28. The broad spectrum light from the short wavelength lamp 25 is condensed by the condenser lens 26 to one focal point in an opening of the pinhole plate 28. The pinhole plate 28 is a plate formed by, for example, vapor depositing chromium onto an optical glass member, excluding an opening thereof.

The wavelength selection filter 27 disposed between the condenser lens 26 and the pinhole plate 28 is a wavelength filter that can select narrowband light around a particular wavelength (e.g., 193 nm, 365 nm, and the like). The wavelength selection filter 27 can also select a plurality of wavelength bands—not just one wavelength band. The light that has become a point light source owing to the pinhole plate 28 proceeds to the collimator lens 31. The point light source that passes through the pinhole plate 28 becomes parallel light with a required diameter, owing to the collimator lens 31, and that parallel light then enters the master template MTP and the replica template RTP.

Namely, the sixth replica template inspection apparatus 150 can additionally perform inspections at, for example, wavelengths of 193 nm and 365 nm. If the wavelength varies, then aspects of the scattered lights SL from those defects DF will vary as a function of the shapes of the defects DF, the sizes of the defects DF and the like. Thus, multiwavelength inspection makes it possible for the computer CP to determine properties such as the shapes of the defects DF and the material properties (in the case of foreign matter contamination) of the defects DF. Furthermore, it is also possible to observe the 193 nm and 365 nm wavelengths simultaneously; alternatively, the 193 nm and 365 nm wavelengths may be observed at different times.

Furthermore, in the case of broadband spectrum light in the range of 193-400 nm, the wavelength selection filter 27 can also select light of a spectral width, for example, wavelengths in the range of 250-350 nm, by extracting the desired band from the broadband spectrum light. There are also cases wherein the solid state laser 21 used in FIG. 11 generates laser specific scattering noise, called speckles. By virtue of the light of the spectral width—which is the light of the desired band extracted from the broadband spectrum light—entering the master template MTP and the replica template RTP, the speckles can also be eliminated.

Furthermore, it is also possible to radiate light of a short wavelength, such as 193 nm, and to observe "fluorescence" at a longer wavelength. This is because fluorescence is often generated when foreign matter (e.g., an organic substance) that absorbs 193 nm light adheres as one of the defects DF.

In addition, instead of the two dimensional photosensor SE, such as a CCD, the sixth replica template inspection apparatus 150 uses the time delay and integrating sensor TDI, which is a two dimensional line sensor. By integrating the electrical charge across the number of integrated stages in the travel direction of the sample, the time delay and integrating sensor TDI improves sensitivity and attenuates noise commensurate with the line sensor's number of stages. Because the scattered lights SL from the defects DF are detected as relatively small luminous energies, it is effective to use the time delay and integrating sensor TDI particularly when the luminous energies of the scattered lights SL are small. Furthermore, the time delay and integrating sensor TDI requires that the movement velocity of a table 51 is constant. In addition, it is necessary to synchronize the movement velocity of the table 51 and the image capture timing.

<Structure of Another Replica Template Inspection Apparatus>

Although not shown in particular, a system may be adopted wherein light of a short wavelength enters from an observation optical system via a beam splitter, as in an epi-illuminated microscope. In such a case, plane waves of a wavelength less than, for example, 193 nm, may be caused to pass through an objective of an observation optical system and then to enter the master template MTP and the replica template RTP. At this time, if none of the defects DF are present in the replica template RTP, then the incident light transmits through the master template MTP and the replica template RTP only. If the defects DF are present in the replica template RTP, then the scattered lights are generated at those portions such that they reflect in the incident direction at a scattering angle of 90° or greater and therefore can be observed by the observation optical system.

Furthermore, the base material of the replica template RTP is not limited to quartz glass, and may be some other glass as long as the base material is transparent to the ultraviolet light UV and the inspection light.

<Relationship Between Defect/Waste Particle Size and Scattered Light Intensity>

Figure 17:
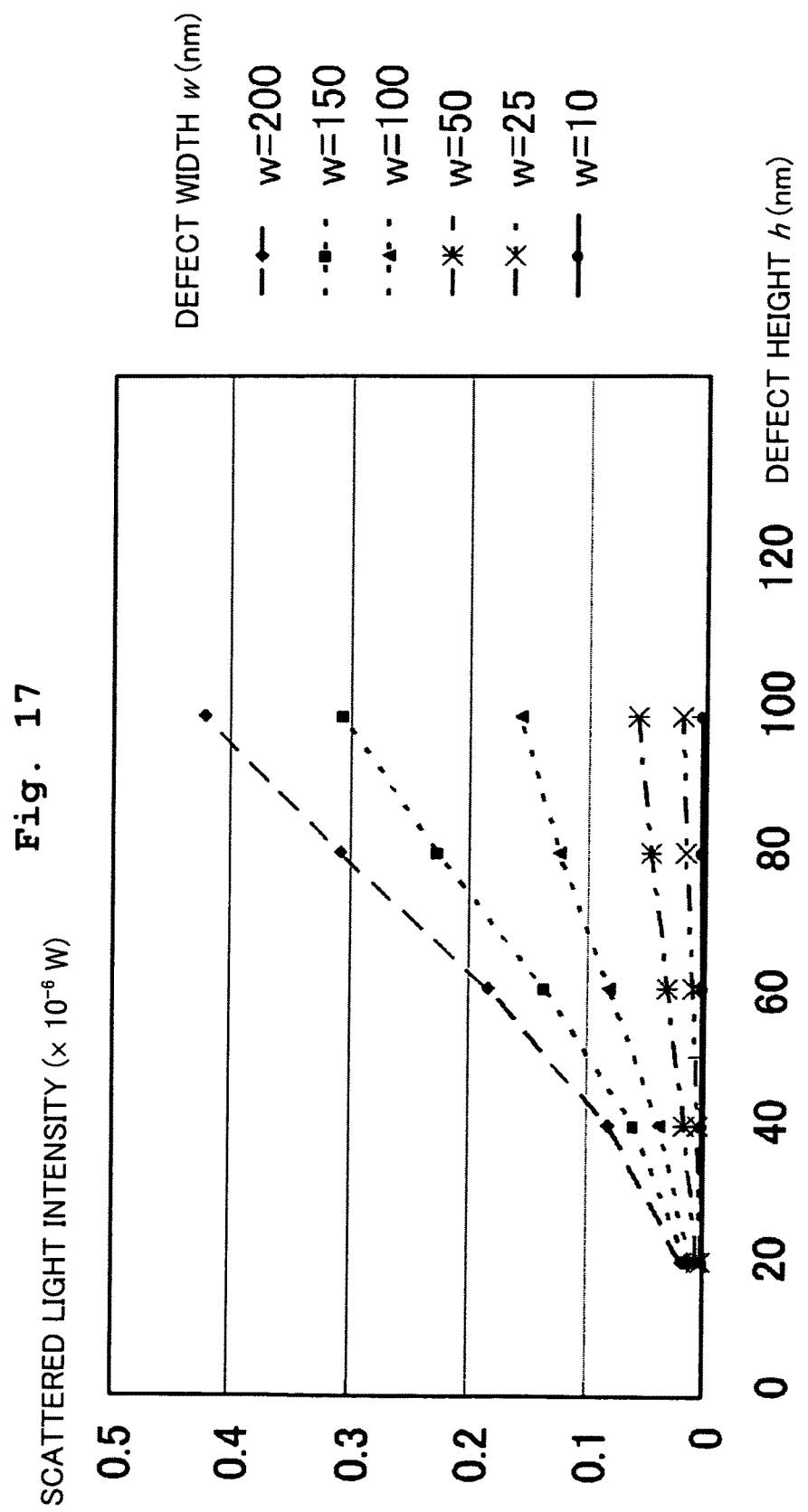
FIG. 17 is a graph that shows the relationship between template defect size and scattered light intensity.

FIG. 17 graphs the simulation results, which show the relationship between template defect size and scattered light SL intensity. The simulation results correspond to the results obtained by using the second replica template inspection apparatus 110 in FIG. 12 to detect the scattered lights SL.

In FIG. 17, the ordinate represents the scattered light intensity (W, i.e., watts) and the abscissa represents the defect height h. The defects DF are quadrangular prisms with a fixed length of 1,000 nm and varying widths w and heights h. It is evident that the greater the volume of the defect, the greater the intensity of the scattered light SL. The laser light from the inspection light source part 20N has a wavelength of 193 nm and is linearly polarized such that the directions of the electric field of the laser light and the longitudinal directions of the defects DF are parallel. The laser light is radiated with a radiation intensity of 1 W to a surface area of the replica template RTP that is 1 mm square.

Figure 18:
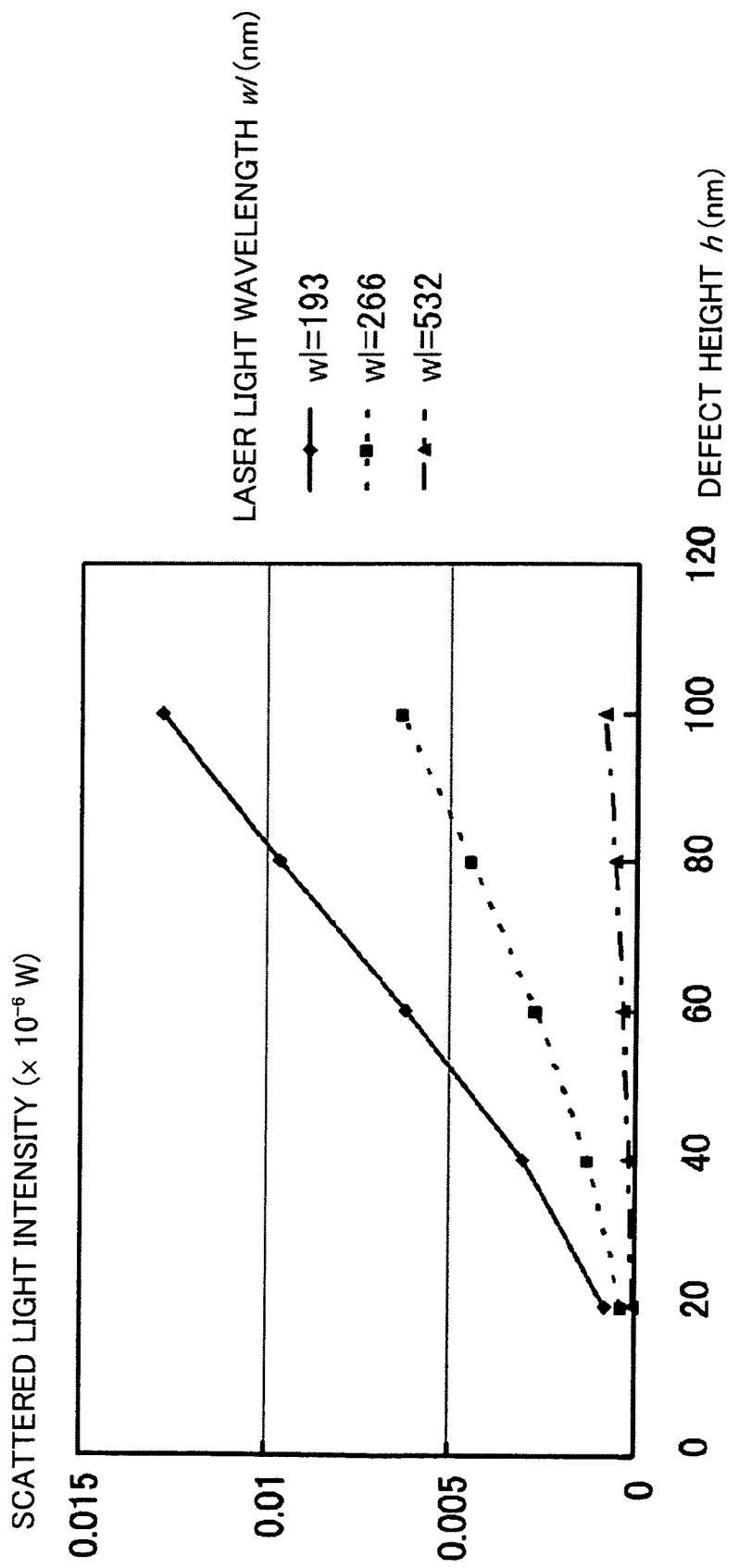
FIG. 18 is a graph that shows the relationship between laser light wavelength and scattered light intensity.

FIG. 18 graphs the simulation results, which show the relationship between the wavelength of the laser light from the inspection light source part 20N and the intensity of the scattered light SL. The simulation results correspond to the results obtained by using the second replica template inspection apparatus 110 in FIG. 12 to detect the scattered lights SL.

In FIG. 18, the ordinate represents the scattered light intensity (W, i.e., watts) and the abscissa represents the defect height h. The defects DF of the replica template RTP have a length of 1,000 nm, a width w of 20 nm, and various heights h. If a wavelength wl of the laser light from the inspection light source part 20N is 532 nm, then the intensities of the scattered lights SL will be low; furthermore, if the wavelength wl of the laser light is 266 nm, then the intensities of the scattered lights SL will increase. It is evident from FIG. 18 that, if the wavelength of the laser light halves, then the intensity of the scattered light SL increases by fourfold or greater. It is evident that, if the wavelength wl of the laser light is 193 nm, then the intensities of the scattered lights SL increase even further. Consequently, it is preferable that the wavelength of the laser light from the inspection light source part 20N is as short as possible. Furthermore, the laser light from the inspection light source part 20N is linearly polarized such that the directions of the electric field of the laser light and the longitudinal directions of the defects DF are parallel; furthermore, the laser light is radiated with a radiation intensity of 1 W to a surface area of the replica template RTP that is 1 mm square.

Figure 19:
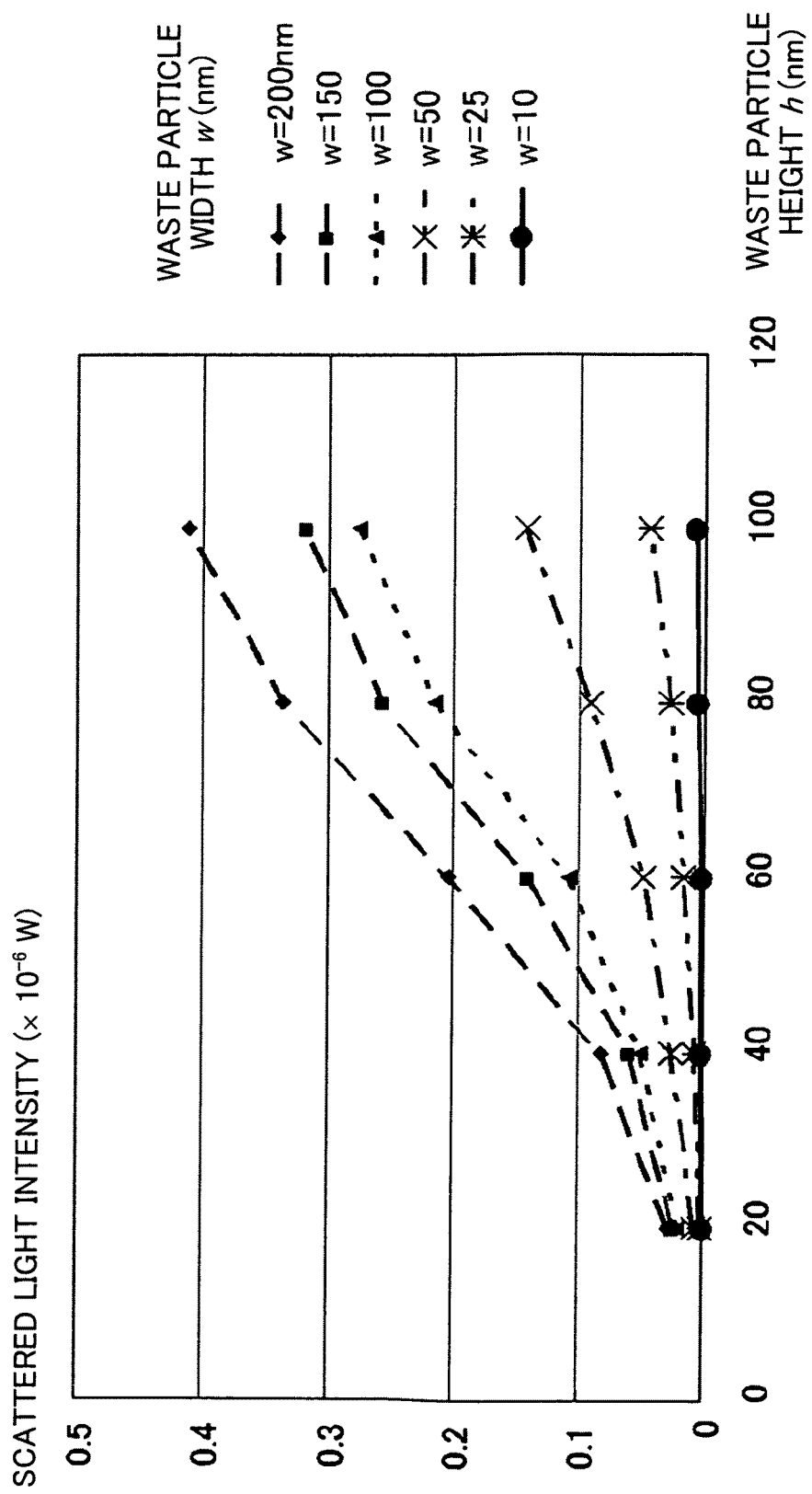
FIG. 19 is a graph that shows the relationship between waste particle size and scattered light intensity.

FIG. 19 graphs the simulation results, which show the relationship between waste particle size and scattered light SL intensity. The simulation results correspond to the results obtained by using the second replica template inspection apparatus 110 in FIG. 12 to detect the scattered lights SL.

In FIG. 19, the ordinate represents the scattered light intensity (W, i.e., watts) and the abscissa represents the waste particle height h. The waste particles PT are quadrangular prisms with a fixed length of 1,000 nm and varying widths w and heights h. It is evident that the larger the waste particle volume, the higher the scattered light SL intensity. The laser light from the inspection light source part 20N has a wavelength of 193 nm and is linearly polarized such that the directions of the electric field of the laser light and the longitudinal directions of the waste particles PT are parallel. The laser light is radiated with a radiation intensity of 1 W to a surface area of the replica template RTP that is 1 mm square.

Figure 20:
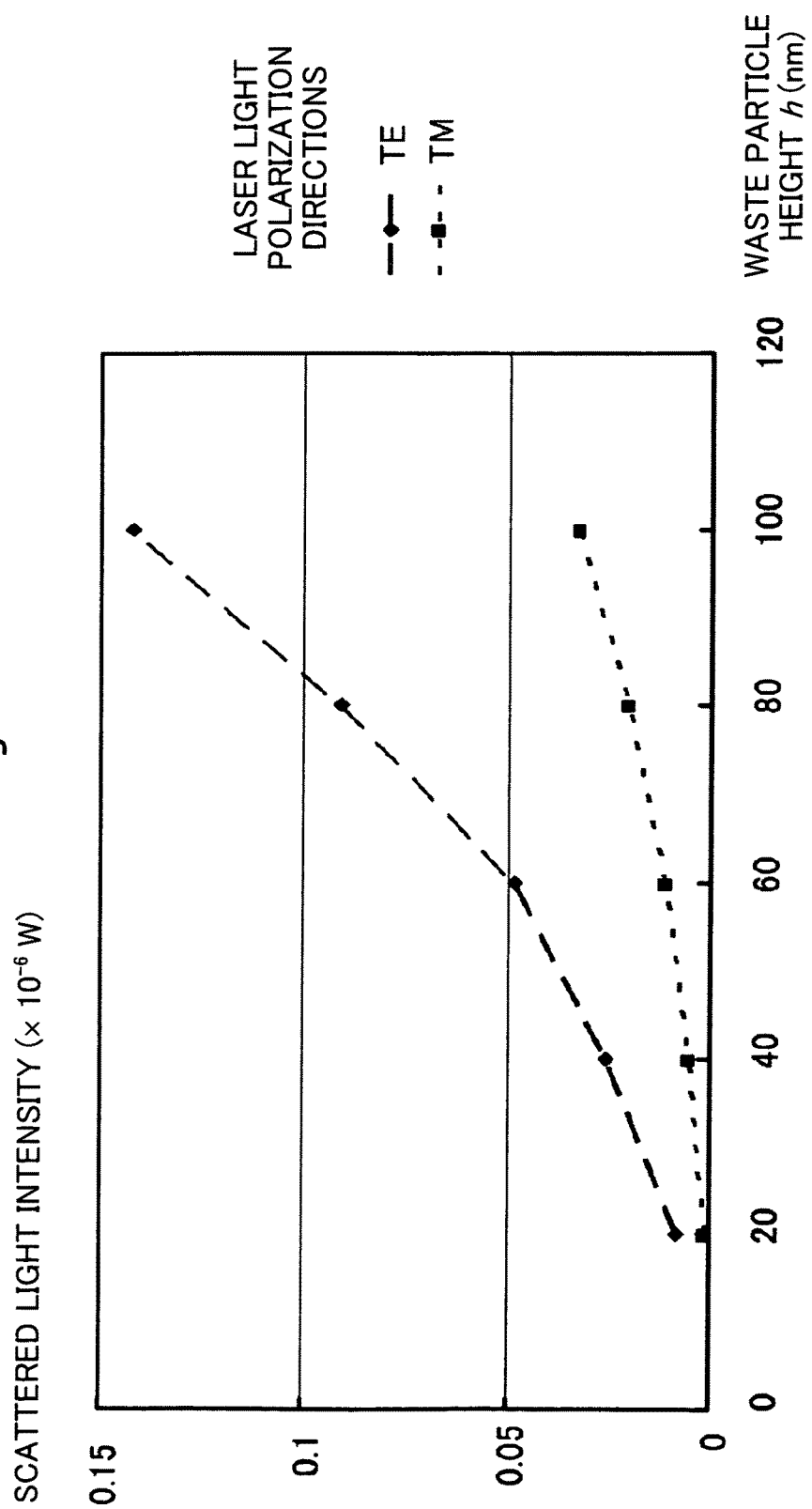
FIG. 20 is a graph that shows the relationship between waste particle size and scattered light intensity.

FIG. 20 graphs the simulation results, which show the relationship between the polarization directions of the laser light from the inspection light source part 20N and the scattered light SL intensity. The simulation results correspond to the results obtained by using the second replica template inspection apparatus 110 in FIG. 12 to detect the scattered lights SL.

In FIG. 20, the ordinate represents the scattered light intensity (W, i.e., watts) and the abscissa represents the waste particle height h. The waste particles PT are quadrangular prisms with a fixed length of 1,000 nm, a fixed width w of 50 nm, and varying heights h. The laser light from the inspection light source part 20N has a wavelength of 193 nm and is linearly polarized; furthermore, the laser light is radiated with a radiation intensity of 1 W to a surface area of the replica template RTP that is 1 mm square. TE indicates the case wherein the polarization directions (i.e., the electric field directions) of the laser light are parallel to the longitudinal directions of the waste particles PT, and TM indicates the case wherein the polarization directions are orthogonal to the longitudinal directions of the waste particles PT. Based on these results, the scattered light SL intensity increases in the case of linear polarization, wherein the polarization directions are parallel to the longitudinal directions of the waste particles PT; consequently, it can be seen that the size and directions of the waste particles PT can be identified by using two mutually orthogonal linearly polarized laser lights.

<Structure of the Stage 40>

Figure 21:
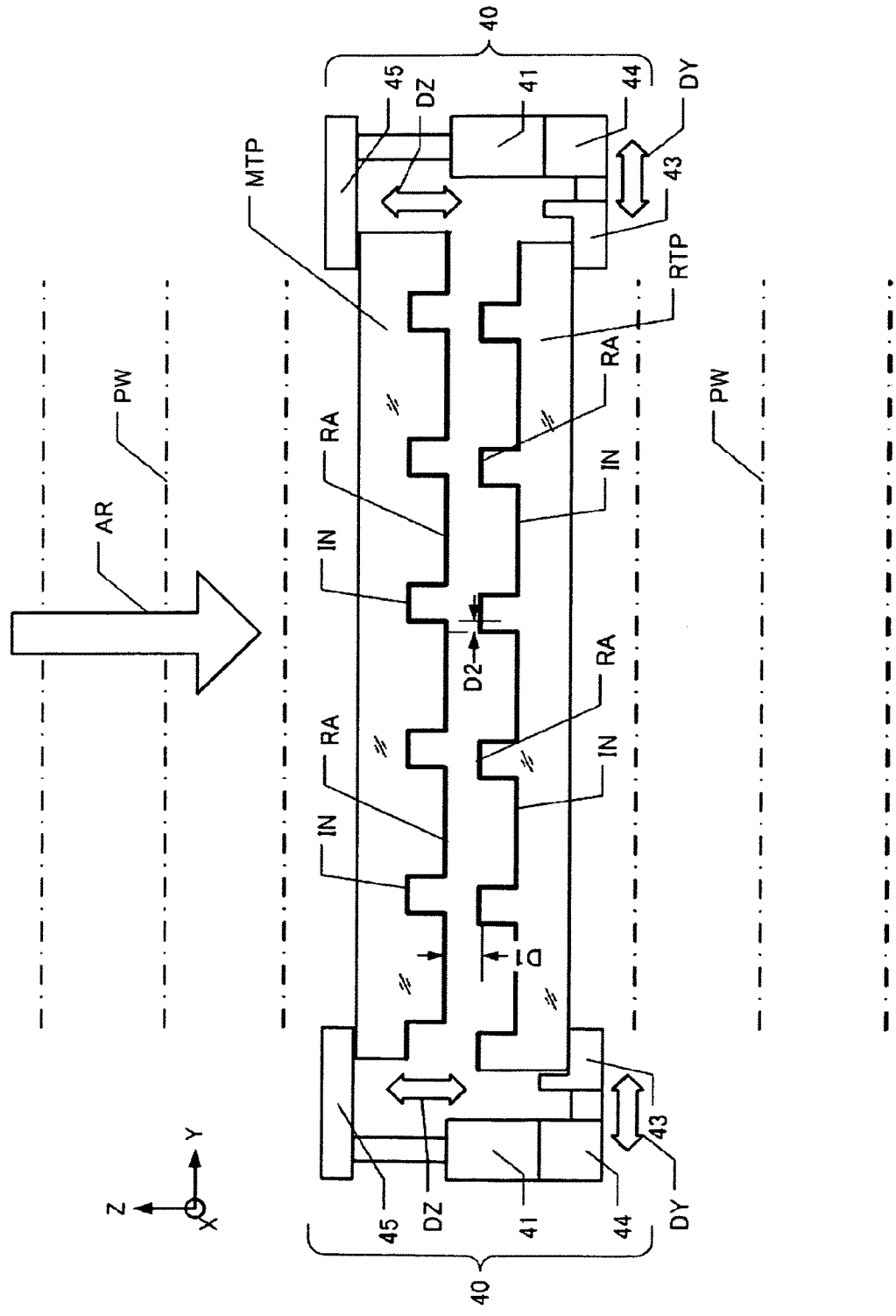
FIG. 21 is an enlarged cross sectional view of a stage 40 of the master template MTP and the replica templates RTP.

FIG. 21 is an enlarged cross sectional view of the vicinity of the master template MTP and the replica template RTP disposed in any one of the apparatuses from the first replica template inspection apparatus 100 through the sixth replica template inspection apparatus 150. In FIG. 21, the laser light (i.e., the plane waves PW) from the inspection light source part 20 (refer to FIG. 11) enters the master template MTP and the replica template RTP from the direction indicated by an arrow AR.

The master template MTP and the replica template RTP are held by the stage 40. The master template MTP is held by Z axial movable clamps 45, and the replica template RTP is held by XY axial movable clamps 43. An XY axial extending and contracting part 44 is provided to each of the XY axial movable clamps 43, and a Z axial extending and contracting part 41 is provided to each of the Z axial movable clamps 45. Each of the Z axial extending and contracting parts 41 and the XY axial extending and contracting parts 44 are drive parts, such as piezoelectric devices, that can be driven in nanometer units.

By extending and contracting in the directions indicated by arrows DZ, the Z axial extending and contracting parts 41 can adjust a distance D1 between the protruding areas RA of the master template MTP and the protruding areas RA of the replica template RTP. By extending and contracting in the directions indicated by arrows DY, the XY axial extending and contracting parts 44 can adjust a distance D2 between the protruding areas RA of the master template MTP and the depressed areas IN of the replica template RTP. Although movement is shown only in the Y axial directions in FIG. 21, movement is also possible in the X axial directions; in addition, by varying the amount of extension and contraction of the XY axial extending and contracting parts 44 individually, the replica template RTP can be rotated within the XY plane.

Namely, by adjusting the positions of the master template MTP and the replica template RTP within the XY plane, the XY axial extending and contracting parts 44 can bring about a state wherein the depression/protrusion pattern of the master template MTP and the depression/protrusion pattern of the replica template RTP are opposed to one another (namely, the state wherein the depressed part of one opposes the protruding part of the other).

The distance D1 should be sufficiently small with respect to the line-and-space pattern and the laser light wavelength (e.g., 193 nm). For example, the distance D1 should be less than or equal to the depth of the depression/protrusion pattern. Specifically, it is preferably less than a value in the range of 20 nm to 10 nm. However, there is no need to make the distance D1 so short that the protruding areas RA of the master template MTP and the depressed areas IN of the replica template RTP mate with one another. In addition, a gas, such as air, is present between the master template MTP and the replica template RTP.

The plane waves PW that transmit through the master template MTP are modulated by the depression/protrusion pattern of the master template MTP. These modulated components enter the depression/protrusion pattern of the replica template RTP as is. As shown in FIG. 4 through FIG. 10, the protruding areas RA and the depressed areas IN of the master template MTP and the protruding areas RA and the depressed areas IN of the replica template RTP are the reverse of one another. The modulated components are once again cancelled by the replica template RTP, transmit through the replica template RTP, and re-emerge as the plane waves PW.

FIG. 22 is an enlarged cross sectional view of the vicinity of the master template MTP and the replica template RTP, which has the defects DF, disposed in the first replica template inspection apparatus 100. In FIG. 22, too, the laser light (i.e., the plane waves PW) from the inspection light source part 20 (refer to FIG. 11) enter the master template MTP and the replica template RTP from the direction indicated by the arrow AR.

The plane waves PW of the laser light that transmit through the master template MTP are modulated by the depression/protrusion pattern of the master template MTP. These modulated components enter the depression/protrusion pattern of the replica template RTP as is. The locations at which the protruding areas RA and the depressed areas IN of the master template MTP and the protruding areas RA and the depressed areas IN of the replica template RTP are precisely the reverse of one another become the plane waves PW; however, at the defects DF, namely, where they are not precisely the reverse of one another, the modulated components are not cancelled and the scattered lights SL emerge. If none of the defects DF are present, then the scattered lights SL are not generated from the template. If the defects DF are present, then the first replica template inspection apparatus 100 detects the defect positions as point light sources. With this inspecting method, the inspection of the replica template RTP is completed in a significantly shorter amount of time than in the case wherein the pattern over the entire surface of the replica template RTP is inspected with an electron beam.

As shown in FIG. 21 and FIG. 22, the wavefronts that transmit through the master template MTP can be decomposed into the modulated components and the plane wave components, however the modulated components dissipate at a higher rate when the wavelength is long than when it is short, and consequently the modulated components of the short wavelengths are preserved for a longer period. Consequently, it is better to use a laser light with a wavelength as short as possible, for example, 193 nm, as shown in FIG. 18.

<Structure of Stage 40'>

Figure 23:
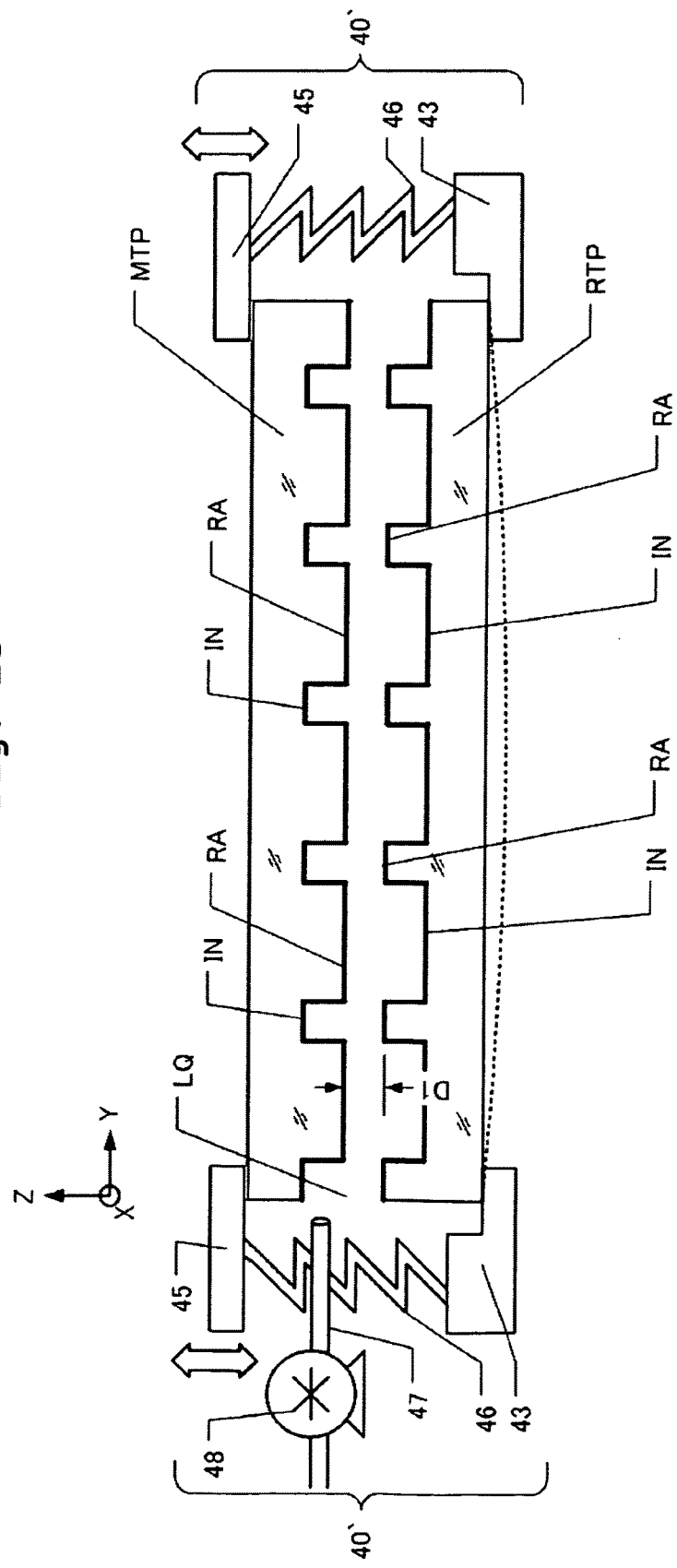
FIG. 23 is an enlarged cross sectional view of a stage 40' of the master template MTP and the replica templates RTP, which is disposed in the first replica template inspection apparatus 100.

FIG. 23 is an enlarged cross sectional view of the vicinity of the master template MTP and the replica template RTP disposed in the first replica template inspection apparatus 100. The stage 40 shown in FIG. 21 and a stage 40' shown in FIG. 23 are structured differently.

In the stage 40' shown in FIG. 23, the master template MTP is held by the Z axial movable clamps 45 and the replica template RTP is held by the XY axial movable clamps 43. Accordion parts 46 are disposed between the XY axial movable clamps 43 and the Z axial movable clamps 45. The area enclosed by the master template MTP, the replica template RTP, and the accordion parts 46 is filled with a liquid LQ. A pipe 47 is provided to one of the accordion parts 46, and a pump 48 is connected to the pipe 47. By adjusting the amount of the liquid LQ supplied by the pump 48, it is possible to adjust the distance D1 between the protruding areas RA of the master template MTP and the protruding areas RA of the replica template RTP to a value in the range of 20 nm to 10 nm or less, for example, 1 nm.

If the replica template RTP warps and the like, as shown by a dotted line in FIG. 23, then the pump 48 reduces the amount of the liquid LQ supplied, which reduces the pressure; thereby, in addition to adjusting the distance D1, the warpage of the replica template RTP can be corrected.

Furthermore, as the liquid LQ, a liquid is selected whose refractive index is different from that of quartz glass, which is the material of the master template MTP and the replica template RTP. This is because if the refractive index of the liquid LQ remaining internally were the same as that of the master template MTP or the replica template RTP, then the wavefronts PW would not be modulated after transmitting through the master template MTP.

<Second Nanoimprinting Apparatus 210>

Figure 24:
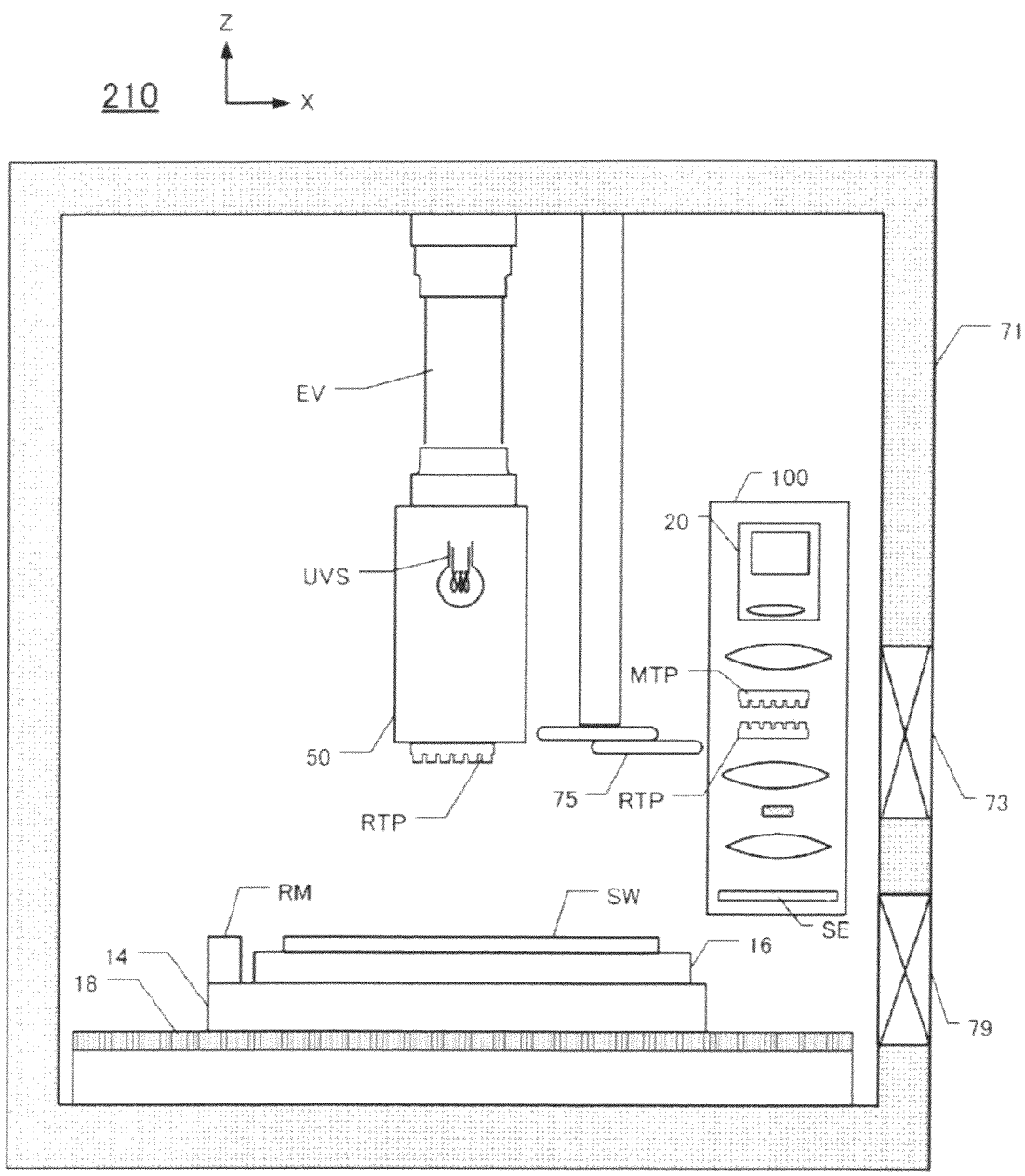

FIG. 24 is a diagram that shows a second nanoimprinting apparatus 210, which has the first replica template inspection apparatus 100 built in. The second nanoimprinting apparatus 210 transfers the depression/protrusion pattern of the replica template RTP to a silicon wafer SW. As shown in FIG. 24, the transferring step is performed inside the chamber 71 to avoid dust and the like. The first replica template inspection apparatus 100 has already been explained, and therefore such explanation is omitted herein.

The second nanoimprinting apparatus 210 comprises the holding part 50, which holds the replica template RTP. The holding part 50 is supported by the pressing elevator EV, which is attached to the ceiling of the chamber 71 of the second nanoimprinting apparatus 210. The pressing elevator EV can move the replica template RTP in the Z directions (i.e., the vertical directions).

Moreover, the silicon wafer SW is vacuum chucked and fixed by the chucking table 16. The silicon wafer SW has a diameter of, for example, approximately 300 mm. The chucking table 16 is supported by the XY stage 14. The XY stage 14 can move in the X axial directions and the Y axial directions. The XY stage 14 is capable of moving in the X axial and Y axial directions with a maximum stroke of, for example, approximately 400 mm, and thereby the depression/protrusion pattern can be transferred from one end to the other end of the silicon wafer SW. The reference mirror RM that extends in the X axial directions (not shown) is fixed to part of the XY stage 14 and the reference mirror RM that extends in the Y axial directions is fixed to another part of the XY stage 14. The XY stage 14 is provided with linear motors 18, which drives the XY stage 14 in the X axial and Y axial directions.

The laser interferometer system (not shown) comprises the X axial laser interferometer, which radiates a laser beam along the X axis to the corresponding reference mirror RM, and the Y axial laser interferometer, which radiates a laser beam along the Y axis to the corresponding reference mirror RM, and measures the X coordinate and the Y coordinate of the XY stage 14. Information about the X coordinate and the Y coordinate measured by the laser interferometer system is supplied to the main control unit 90, which controls the operation of positioning the XY stage 14 using the linear motors 18 while monitoring the supplied coordinates.

In the second nanoimprinting apparatus 210, the pressing elevator EV applies pressure such that the replica template RTP is pressed against the ultraviolet light setting resin PM provided on the wafer SW. Thereby, the resin PM in the gap between the replica template RTP and the wafer SW conforms to the depression/protrusion pattern of the replica template RTP. In this state, the ultraviolet light UV generated by the ultraviolet light source UVS provided inside the pressing elevator EV is radiated to the resin PM, which thereby sets. Subsequently, by separating the replica template RTP from the set resin PM, the depression/protrusion pattern is formed in the set resin PM.

In addition, the second nanoimprinting apparatus 210 comprises a transport robot 75, which can transport the replica template RTP and the silicon wafer SW. The chamber 71 of the second nanoimprinting apparatus 210 comprises a gate 73, which is for the master template MTP and the replica template RTP, and the gate 79, which is for the silicon wafer SW. The master template MTP and the replica template RTP can be attached to the first replica template inspection apparatus 100 inside the chamber 71 via the gate 73. When the first replica template inspection apparatus 100 completes its inspection of the replica template RTP, the transport robot 75 transports the replica template RTP from the first replica template inspection apparatus 100 to the holding part 50.

Because the second nanoimprinting apparatus 210 has the first replica template inspection apparatus 100 built in, the second nanoimprinting apparatus 210 can inspect for defects DF occurring in the replica template RTP with high precision and in a short time, both prior to the start of production of the semiconductor devices and each time a prescribed number of wafers is produced during production. In addition, because the first replica template inspection apparatus 100 is disposed in the chamber 71 and the replica template RTP is attached to the holding part 50 inside the chamber 71, the risk that the waste particles PT, such as dust, will adhere to the replica template RTP is reduced.

<Nanoimprinting System 300>

Figure 25:
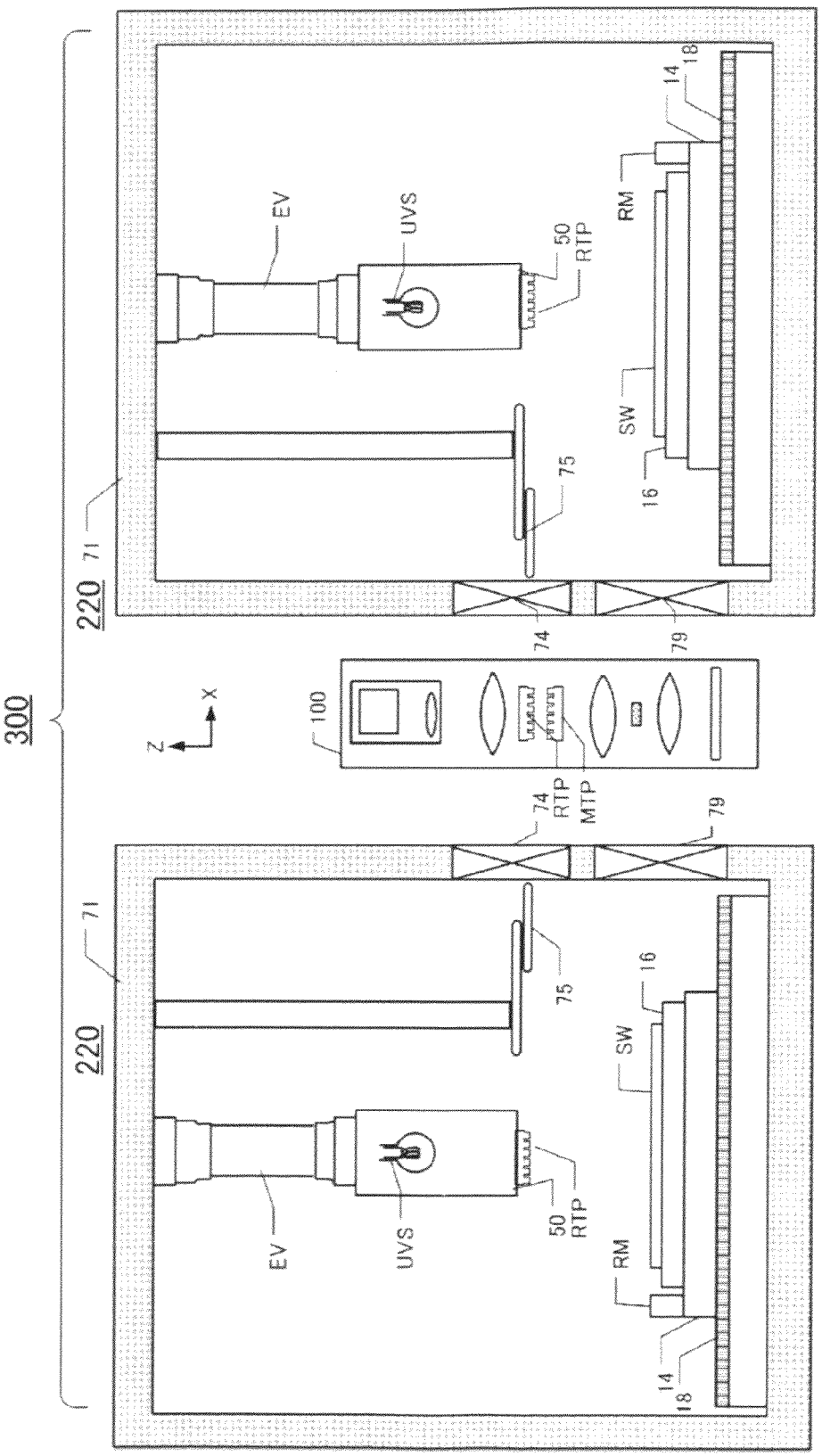
FIG. 25 is a conceptual diagram that shows a nanoimprinting system 300.

FIG. 25 is a conceptual diagram that shows a nanoimprinting system 300, which includes two third nanoimprinting apparatuses 220 and one of the first replica template inspection apparatuses 100. Each of the third nanoimprinting apparatuses 220 comprises the second nanoimprinting apparatus 210 explained in FIG. 24—with the exception of the first replica template inspection apparatus 100—and therefore a detailed explanation is omitted herein. In addition, because the first replica template inspection apparatus 100 has already been explained, an explanation thereof is omitted herein.

In addition, each of the third nanoimprinting apparatuses 220 comprises the transport robot 75, which can transport the replica template RTP and the silicon wafer SW. The chamber 71 of each of the third nanoimprinting apparatuses 220 has a gate 74, which is for the replica template RTP. The transport robot 75 transports the replica template RTP from the first replica template inspection apparatus 100 to the holding part 50 via the gate 74. In addition, the transport robot 75 can load the silicon wafer SW into and unload the silicon wafer SW from the third nanoimprinting apparatus 220 via the gate 79.

As shown in FIG. 25, two of the third nanoimprinting apparatuses 220 are provided, each of which transfers the depression/protrusion pattern of one of the replica templates RTP to the setting resin PM formed on the corresponding silicon wafer SW. Using two of the replica templates RTP thereby makes it possible to double the production volume of the semiconductor devices, which are formed on the silicon wafers SW. Furthermore, the replica templates RTP attached to the holding parts 50 of the two third nanoimprinting apparatuses 220 are transported by the transport robots 75 after the single first replica template inspection apparatus 100 confirms in a short time that the defects DF are not present. Accordingly, the production of defect-free semiconductor devices doubles. In FIG. 25, two of the third nanoimprinting apparatuses 220 are disposed; however, it is obvious that three or more of the third nanoimprinting apparatuses 220 may be disposed.

<Semiconductor Device Manufacturing Method>

Figure 26:
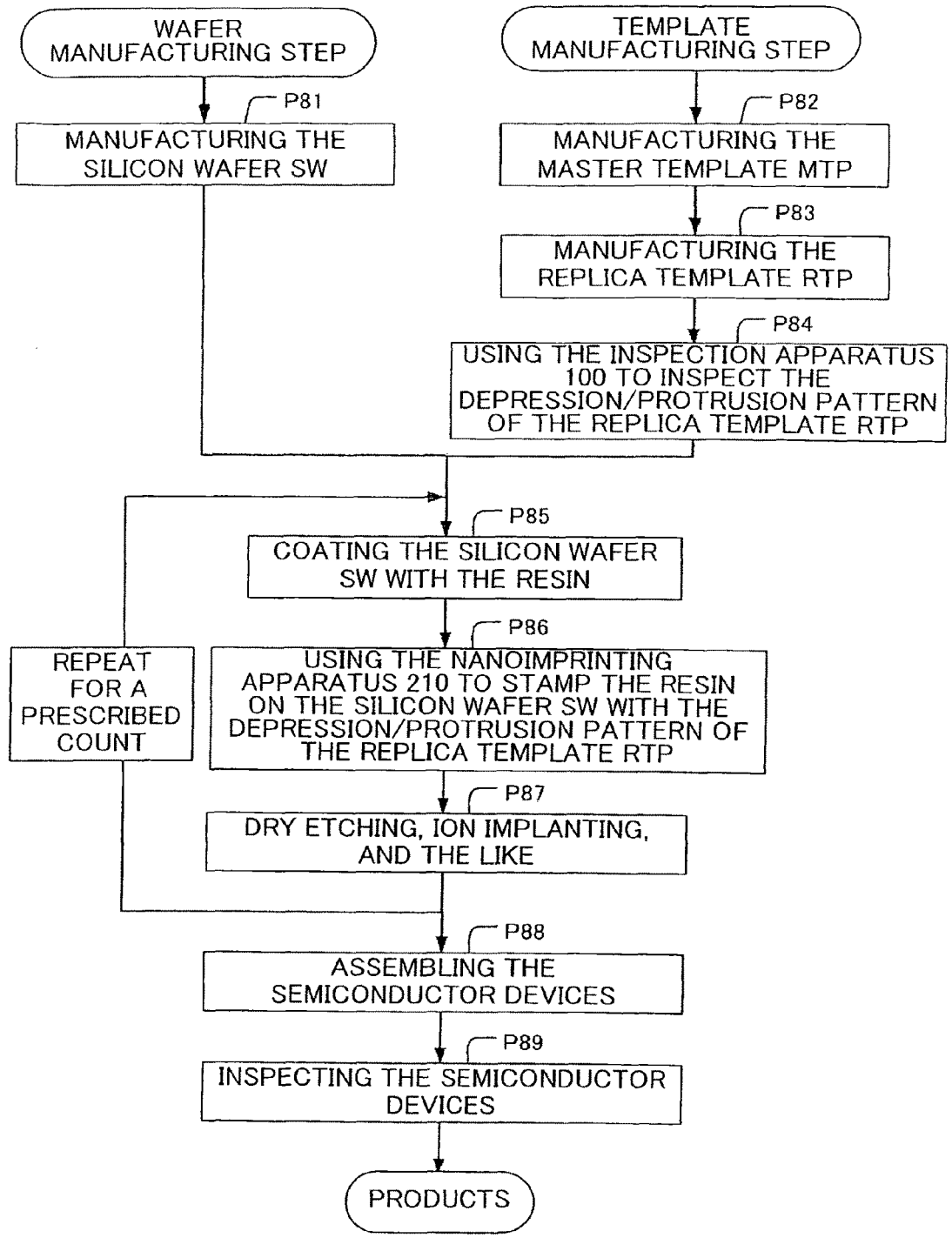
FIG. 26 is a flow chart that depicts a semiconductor device manufacturing method.

An example of an embodiment of a semiconductor device (e.g., memory, an LSI, or the like) manufacturing method according to the present embodiment will now be explained. FIG. 26 is a flow chart that shows one example of the semiconductor device manufacturing method of the present invention. An example will be explained wherein the second nanoimprinting apparatus 210 shown in FIG. 24 is used in the manufacture of semiconductor devices.

In a step P81, the silicon wafer SW is manufactured by cutting a wafer from a silicon ingot and then polishing the wafer.

Moreover, in a step P82, an electron beam or the like is used to manufacture the master template MTP based on design data. Furthermore, the master template MTP is inspected to determine whether it was manufactured in accordance with the design data.

In a step P83, the replica template RTP is manufactured by the steps explained referencing FIG. 4 through FIG. 10.

In a step P84, any one of the apparatuses from the first replica template inspection apparatus 100 through the sixth replica template inspection apparatus 150 explained referencing FIG. 11 through FIG. 16 is used to verify that none of the defects DF are present in the replica template RTP. If none of the defects DF are present, then the replica template RTP is transported to the second nanoimprinting apparatus 210.

In a step P85, the silicon wafer SW is coated with the thermosetting or ultraviolet light setting resin PM, for example, an acrylic resin.

In a step P86, the second nanoimprinting apparatus 210 is used to stamp the resin PM on the silicon wafer SW with the depression/protrusion pattern of the replica template RTP. Thereby, a depression/protrusion pattern that is the reverse of the depression/protrusion pattern of the replica template RTP is formed in the resin PM.

In a step P87, the silicon wafer SW is dry etched using the depression/protrusion pattern in the resin PM as a mask. In addition, steps necessary for the manufacture of semiconductor devices are performed, for example: a thin film forming step (e.g., CVD, sputtering) wherein a dielectric thin film is formed as an insulating layer, a metal thin film is formed as wiring parts or electrode parts, and the like; ion implantation; and the like.

By repeating the steps P85 through P87 for a prescribed count, a plurality of layers are fabricated and semiconductor devices are formed in the silicon wafer SW.

In a step P88, the semiconductor devices formed on the silicon wafer SW are diced one at a time, and then the diced semiconductor devices are assembled such that they are capable of operation.

In a step P89, the assembled semiconductor devices are inspected.

By undergoing the above steps, the semiconductor devices are made into products.

The explanation above assumes that the master template MTP is drawn with an electron beam or the like based on design data—one datum at a time. However, if a grandchild replica template is further produced based on the replica template RTP, then the grandchild replica template will have an identical depression/protrusion pattern to that of the master template MTP. Such a grandchild replica template can be treated as equivalent to the master template MTP and adapted likewise.

The invention claimed is:

1. A nanoimprinting apparatus, comprising:
    a master template which has a depression/protrusion pattern;
    a replica template which is manufactured from the master template by an imprinting method;
    an inspection light source part which radiates inspection light of plane waves;
    a stage configured to dispose the master template and the replica template so as to be in close proximity with each other;
    a detection part which detects light of a component different from the plane waves, the light of the component being generated by the plane wave transmitting through the master template and the replica template;
    a transport unit which transports the replica template from the stage;
    a holding part which receives the transported replica template from the transport unit and holds the transported replica template;
    a substrate mounting platform which is disposed opposing the replica template held by the holding part and whereon a substrate is mounted, the substrate being coated with a liquid resin;
    a pressing part which presses at least one of the replica template and the substrate such that the resin is stamped with the depression/protrusion pattern;
    an optical system, which is disposed between the detection part, on one side; and the master template and the replica template, on an other side, and in a radiation direction of the inspection light; and
    a light shielding member, which is disposed at a pupil position of the optical system and which blocks the plane waves.

2. A nanoimprinting system, comprising:
    a master template which has a depression/protrusion pattern;
    a replica template which is manufactured from the master template by an imprinting method;
    an inspection light source part which radiates inspection light of plane waves;
    a stage configured to dispose the master template and the replica template so as to be in close proximity with each other;
    a detection part which detects light of a component different from the plane waves, the light of the component being generated by the plane wave transmitting through the master template and the replica template;
    a transport unit which transports the replica template from the stage;
    two holding parts which receive two pieces of the transported replica template respectively from the transport unit and which hold the transported replica templates;
    two substrate mounting platforms which are disposed opposing the two pieces of the replica templates held by the two holding parts and whereon substrates are mounted, each of the substrates being coated with a liquid resin;
    two pressing parts each of which presses at least one of the replica template and the substrate such that the resin is stamped with the depression/protrusion pattern, and
    an optical system which is disposed between the detection part, on one side, and the master template and the replica template, on an other side, and in a direction different from a radiation direction of the inspection light.

3. The nanoimprinting apparatus according to claim 1, wherein the stage can adjust a distance between the master template and the replica template.

4. The nanoimprinting apparatus according to claim 1, wherein the stage fills a space between the master template and the replica template with a liquid.

5. The nanoimprinting apparatus according to claim 4, wherein a refractive index of the liquid is different from a refractive index of the master template or a refractive index of the replica template.

6. The nanoimprinting apparatus according to claim 1, wherein the inspection light is light of a first short wavelength, which is shorter than wavelengths of visible light, and a second short wavelength, which is different from the first short wavelength.

7. The nanoimprinting apparatus according to claim 1, wherein the light of the component different from the plane waves includes a spherical wave component.

8. The nanoimprinting system according to claim 2, wherein the stage can adjust a distance between the master template and the replica template.

9. The nanoimprinting system according to claim 2, wherein the stage fills a space between the master template and the replica template with a liquid.

10. The nanoimprinting system according to claim 9, wherein a refractive index of the liquid is different from a refractive index of the master template or a refractive index of the replica template.

11. The nanoimprinting system according to claim 2, wherein the inspection light is light of a first short wavelength, which is shorter than wavelengths of visible light, and a second short wavelength, which is different from the first short wavelength.

12. The nanoimprinting system according to claim 2, wherein the light of the component different from the plane waves includes a spherical wave component.

13. A nanoimprinting apparatus, comprising:
    a master template which has a depression/protrusion pattern;
    a replica template which is manufactured from the master template by an imprinting method;
    an inspection light source part which radiates inspection light of plane waves;
    a stage configured to dispose the master template and the replica template so as to be in close proximity with each other;
    a detection part which detects light of a component different from the plane waves, the light of the component being generated by the plane wave transmitting through the master template and the replica template;
    a transport unit which transports the replica template from the stage;
    a holding part which receives the transported replica template from the transport unit and holds the transported replica template;

a substrate mounting platform which is disposed opposing the replica template held by the holding part and whereon a substrate is mounted, the substrate being coated with a liquid resin;

a pressing part which presses at least one of the replica template and the substrate such that the resin is stamped with the depression/protrusion pattern; and an optical system which is disposed between the detection part, on one side, and the master template and the replica template, on an other side, and in a direction different from a radiation direction of the inspection light.

* * * * *